US011022544B2

(12) United States Patent
Crosson et al.

(10) Patent No.: US 11,022,544 B2
(45) Date of Patent: *Jun. 1, 2021

(54) GENERATING SIGNATURES BASED ON SENSING GAS CONCENTRATION CONDITIONS

(71) Applicant: Sparrow Detect, Inc., Pleasanton, CA (US)

(72) Inventors: Eric R. Crosson, Livermore, CA (US); David A. Fisher, Menlo Park, CA (US)

(73) Assignee: Sparrow Detect, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/825,460

(22) Filed: Mar. 20, 2020

(65) Prior Publication Data

US 2020/0217787 A1 Jul. 9, 2020

Related U.S. Application Data

(63) Continuation-in-part of application No. 15/909,909, filed on Mar. 1, 2018, now Pat. No. 10,724,946.

(60) Provisional application No. 62/962,975, filed on Jan. 18, 2020, provisional application No. 62/560,235, filed on Sep. 19, 2017.

(51) Int. Cl.
*G01N 21/31* (2006.01)
*G01N 33/00* (2006.01)

(52) U.S. Cl.
CPC ......... *G01N 21/31* (2013.01); *G01N 33/0047* (2013.01)

(58) Field of Classification Search
CPC .... G01N 21/31; G01N 33/0047; G01N 21/39; G01N 2021/391; G01N 2021/393; H01S 5/06835; H01S 5/146; H01S 5/0622
See application file for complete search history.

(56) References Cited

U.S. PATENT DOCUMENTS

| 4,793,709 A | 12/1988 | Jabr et al. |
| 5,528,040 A | 6/1996 | Lehmann |
| 5,793,485 A | 8/1998 | Gourley |

(Continued)

FOREIGN PATENT DOCUMENTS

WO WO 2017/108726 6/2017

OTHER PUBLICATIONS

Richard Engeln, Giel Berden, Rudy Peeters, and Gerard Meijer, "Cavity enhanced absorption and cavity enhanced magnetic rotation spectroscopy", Review of Scientific Instruments, vol. 69, No. 11, p. 3763, Nov. 1998.

(Continued)

*Primary Examiner* — Jamil Ahmed
(74) *Attorney, Agent, or Firm* — Brian R. Short

(57) ABSTRACT

Apparatuses, methods, and systems for generating signatures based on sensing one or more gas concentration conditions are disclosed. One method includes sensing, by one or more sensors, levels of a gas over time for a plurality of gas concentration conditions, receiving, by a controller, the sensed levels of gas over time for the plurality of gas concentration conditions, and generating, by the controller, a plurality of signatures, wherein one or more signatures is generated for one or more gas concentration conditions based on the sensed levels of gas over time, and determining whether to take action or not to take action.

21 Claims, 31 Drawing Sheets

(56) References Cited

U.S. PATENT DOCUMENTS

| | | | |
|---|---|---|---|
| 5,912,740 | A | 6/1999 | Zare et al. |
| 6,084,682 | A | 7/2000 | Zare et al. |
| 6,504,145 | B1 | 1/2003 | Romanini et al. |
| 6,628,695 | B1 * | 9/2003 | Aldaz ............... H01S 5/18388 372/92 |
| 6,795,190 | B1 | 9/2004 | Paul et al. |
| 7,450,240 | B2 | 11/2008 | Morville et al. |
| 7,538,881 | B2 | 5/2009 | Ye et al. |
| 7,936,463 | B2 | 5/2011 | Kiesel et al. |
| 8,539,816 | B2 | 9/2013 | Kachanov et al. |
| 8,659,759 | B2 | 2/2014 | Koulikov et al. |
| 8,885,167 | B2 | 11/2014 | Kachanov et al. |
| 9,194,742 | B2 | 11/2015 | Kachanov et al. |
| 9,304,080 | B2 | 4/2016 | Kachanov et al. |
| 2010/0055802 | A1 | 3/2010 | Zare et al. |

OTHER PUBLICATIONS

Anthony E. Siegman (1986) Lasers, Sausalito, California, University Science Books, ISBN 0-935702-11-3, pp. 626-638, pp. 744-764.

PCT Notification of Transmittal of the International Search Report and the Written Opinion of the International Searching Authority, or the Declaration; dated Nov. 5, 2018; PCT/US18/49631 having an international filing date of Sep. 6, 2018.

English Translation of German Office Action for German Patent Application No. 112018005289.3 (112018005289T5), Titled: Tunable Light Source Cavity Detection Using a Plurality of Axial-Plus-Transverse Modes, dated Sep. 4, 2020.

* cited by examiner

Detecting a substance (gas) within an optical cavity based on at least one of an intensity, an amplitude, a phase, or an amplitude and phase of sensed electro-magnetic radiation emanating from the optical cavity at one or more of a plurality of wavelengths while the optical cavity receives a beam of electro-magnetic radiation

1910

Recording, by a controller, information related to the detected substance (gas)

1920

Recording, by the controller, an event or action relating to the detected substance (gas)

1930

Describing or representing in terms of a parameter or parameters (parameterizing), by the controller, the recorded information and an action or event related to the detected substance (gas).

1940

Recording, by the controller, the parameterized information in a database

Sensing, by one or more sensors, levels of a gas over time for a plurality of gas concentration conditions

2910

Receiving, by a controller, the sensed levels of gas over time for the plurality of gas concentration conditions

2920

Generating, by the controller, a plurality of signatures, wherein one or more signatures is generated for one or more gas concentration conditions based on the sensed levels of gas over time

GENERATING SIGNATURES BASED ON SENSING GAS CONCENTRATION CONDITIONS

RELATED APPLICATIONS

This patent application claims priority to US Provisional Patent Application Ser. No. 62/962,975 filed Jan. 18, 2020, this patent application is a continuation-in-part (CIP) of U.S. patent application Ser. No. 15/909,909, filed Mar. 1, 2018, which claims priority to US Provisional Patent Application Ser. No. 62/560,235 filed Sep. 19, 2017, which are all herein incorporated by reference.

FIELD OF THE DESCRIBED EMBODIMENTS

The described embodiments relate generally to gas detection. More particularly, the described embodiments relate to systems, methods and apparatuses for generating signatures based on sensing one or more gas concentration conditions.

BACKGROUND

There are many applications and markets today where much effort is being invested to develop sensor technologies that have greater performance in terms of sensitivity (parts per million or billion) and specificity (unambiguously detecting identified molecules) while offering the economics needed to deploy in a large scale while providing both qualitative and quantitative data to improve safety, their infrastructure and to better the environment. One example of such a need is around natural gas sensing (methane), a common energy source around the world. In the United States there are over 68 million homes and over 6 million buildings and thousands of factories that rely on natural gas. This gas is delivered via over 2.4 million miles of main gas pipelines having distributing pipes extending to homes/buildings and factories. This is a common means of distributing energy in major cities around the world. As with any infrastructure, the pipes continue to age and are prone to hazardous leaks. Natural gas is a highly combustible odorless and colorless hydrocarbon gas largely composed of methane. Gas leaks present a serious safety and environment hazard and much effort has been invested in developing higher sensitivity and specificity sensors. The need to deploy sensors extending to residential homes and buildings has placed price/performance criteria on sensors that are not currently satisfied by existing technologies. The primary performance concerns with existing commercial sensors are that they do not have specificity and hence generate false positives to common household agents; level of detection is not sufficient and the range of sensing is limited.

The Oil and Gas industry also utilize a wide variety of gases that present safety and environmental issues if not widely monitored for leaks. In the United State, Leak Detection And Repair (LDAR) programs are required as part of the Federal Regulations. A LDAR program is a facility's system of procedures used to locate and repair leaking components (e.g., valves, pumps, connectors, compressors, and agitators) to minimize fugitive Volatile Organic Compounds (VOC) and Hazardous Air Pollutants (HAP) emissions including but not limited to methane.

It is desirable to have methods, apparatuses, and systems for generating signatures based on sensing one or more gas concentration conditions.

SUMMARY

An embodiment includes a method. The method includes sensing, by one or more sensors, levels of a gas over time for a plurality of gas concentration conditions, receiving, by a controller, the sensed levels of gas over time for the plurality of gas concentration conditions, and generating, by the controller, a plurality of signatures, wherein one or more signatures is generated for one or more gas concentration conditions based on the sensed levels of gas over time.

Another embodiment includes a system. The system includes one or more sensors and a controller. The one or more sensors are operative to sense levels of a gas over time for a plurality of gas concentration conditions. The controller is operative to receive the sensed levels of gas over time for the plurality of gas concentration conditions, and generate a plurality of signatures, wherein one or more signatures is generated for one or more gas concentration conditions based on the sensed levels of gas over time.

Other aspects and advantages of the described embodiments will become apparent from the following detailed description, taken in conjunction with the accompanying drawings, illustrating by way of example the principles of the described embodiments.

BRIEF DESCRIPTION OF THE DRAWINGS

FIG. 19 is a flow chart that includes steps of a method of parameterizing recoded information related to detecting a gas, and an event or action related to the detecting of the gas, according to an embodiment.

FIG. 29 is a flow chart that include steps of a method of generating a plurality of signatures, wherein one or more signatures is generated for one or more gas concentration conditions based on the sensed levels of gas over time, according to an embodiment.

DETAILED DESCRIPTION

The embodiments described include methods, apparatuses, and systems for generating signatures based on sensing one or more gas concentration conditions. Further, at least some embodiments include identifying gas concentration conditions by comparing sensed gas with the signatures. For an embodiment, the sensing is performed by a sensor that includes tunable light source cavity detection using a plurality of allowed axial-plus-transverse modes.

Figure 1:
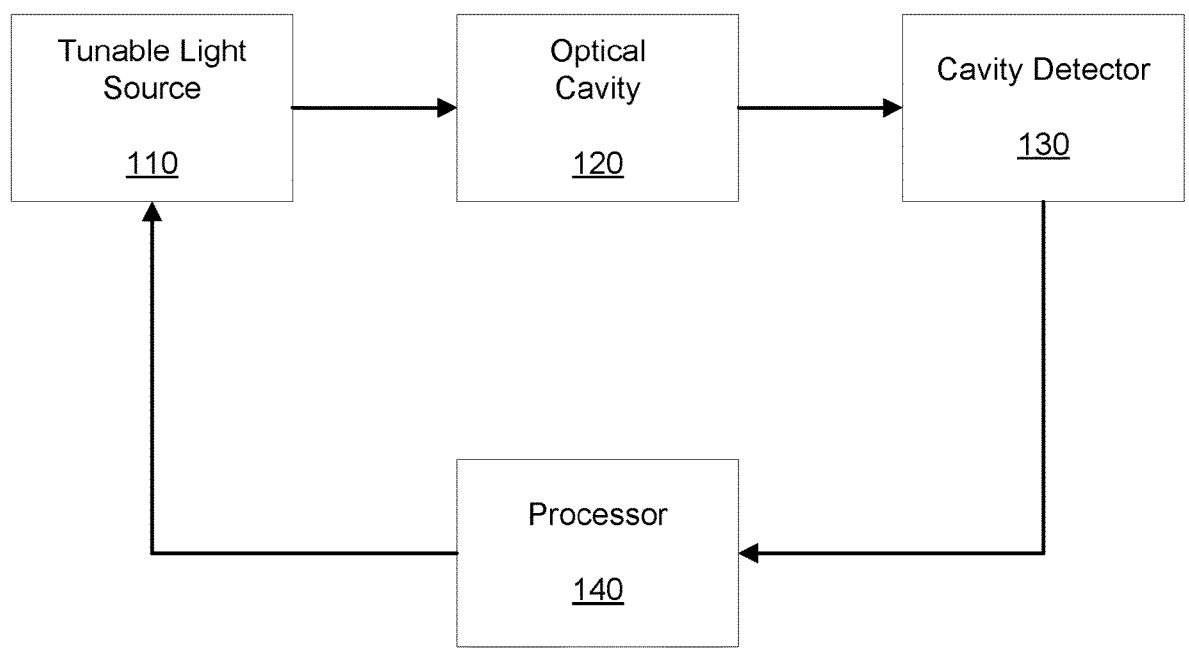
FIG. 1 is a block diagram of a system for detecting a substance, according to an embodiment.

FIG. 1 is a block diagram of a system for detecting a substance (such as, a gas), according to an embodiment. The system includes a tunable light source 110, an optical cavity 120, a cavity detector 130, and a processor 140. For an embodiment, the tunable light source 110 generates a beam of electro-magnetic radiation, wherein a wavelength of the beam of electro-magnetic radiation is tuned to operate at a plurality of wavelengths. The optical cavity 120 receives the beam of electro-magnetic radiation, wherein physical characteristics of the optical cavity 120 define a plurality of allowed axial-plus-transverse electro-magnetic radiation modes, wherein only a subset of the plurality of allowed axial-plus-transverse electro-magnetic radiation modes are excited when the optical cavity 120 receives the beam of electro-magnetic radiation. The cavity detector 130 senses electro-magnetic radiation emanating from the optical cavity 120. The processor 140 operates to receive information relating to the sensed electro-magnetic radiation, and detect the substance (gas) within the optical cavity 120 based on at least one of an intensity, an amplitude, a phase, or an amplitude and phase of the sensed electro-magnetic radiation emanating from the optical cavity 120 at one or more of the plurality of wavelengths while the optical cavity 120 receives the beam of electro-magnetic radiation.

Figure 2:
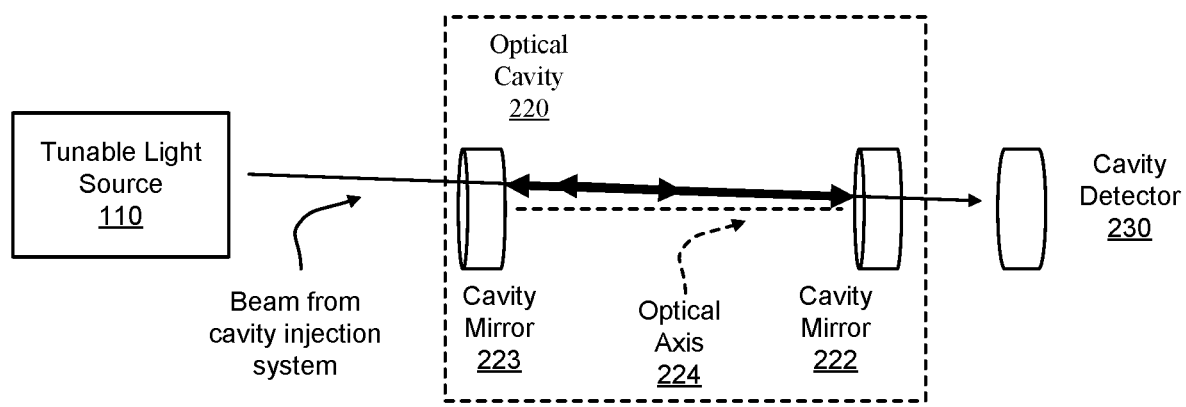
FIG. 2 is a block diagram that includes misalignment of the incoming beam to an axis of the optical cavity.

FIG. 2 is a block diagram that includes misalignment of the incoming beam (of the tunable light source 110) to an axis 224 of an optical cavity 220. For at least some embodiments, the subset of the plurality of the allowed axial-plus-transverse electro-magnetic radiation modes is excited by misaligning the incoming beam of electro-magnetic radiation with the axis 224 of the optical cavity 220. For an embodiment, the subset includes a number greater than one. The optical cavity 220 includes cavity mirrors 223, 222. A cavity detector 230 senses electro-magnetic radiation emanating from the optical cavity 220.

For at least some embodiments, the subset of the plurality of the allowed axial-plus-transverse electro-magnetic radiation modes is excited by mode mismatching a waist size and/or a waist location of the incoming beam of electro-magnetic radiation to the allowed axial-plus-transverse modes that are defined by the optical cavity. For an embodiment, the incoming beam of electro-magnetic radiation comprises more than one transverse mode. For at least some embodiments, the beam of electro-magnetic radiation in the cavity impacts one location on each mirror that defines the cavity.

A first implementation could include cavity-based implementations that utilize the amplitude of a single axial-plus-transverse electro-magnetic radiation mode of the cavity which is enhanced using a single wavelength laser. Further, the absorption of one axial-plus-transverse electro-magnetic radiation mode is quantified, when the single wavelength laser is no longer enhancing (the laser diode is turned off and/or not transmitting electro-magnetic radiation) the axial-plus-transverse electro-magnetic radiation mode of the cavity. A second implementation could utilize a single wavelength laser so that the interaction between the laser and the cavity always excites the entire plurality of allowed axial-plus-transverse electro-magnetic radiation mode defined by the cavity. However, both of these implementations require very precise cavity alignment and very expensive optical components. In contrast, the described embodiments do not require precise cavity alignment and can be configured with low-cost optical components.

As shown, the embodiment of FIG. 1, a tunable light source cavity detection system utilizing multiple wavelengths, using a subset of the plurality of allowed axial-plus-transverse electro-magnetic radiation modes of the cavity, whereby summing the information from a subset of the plurality of allowed axial-plus-transverse electro-magnetic radiation modes while the tunable light source enhances the axial-plus-transverse electro-magnetic radiation modes of the cavity, enables the use of low cost optical components.

Figure 3:
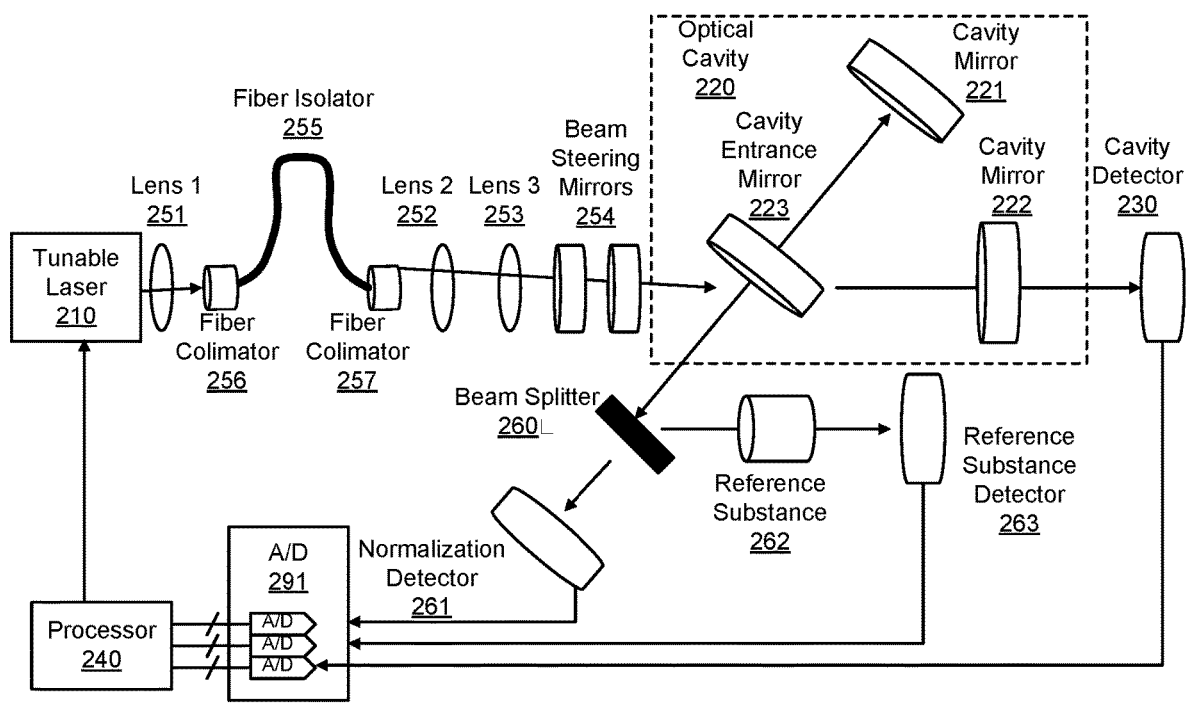
FIG. 3 is a block diagram that includes more detail of a system for detecting a substance, according to an embodiment.

FIG. 3 is a block diagram that includes more detail of a system for detecting a substance, according to an embodiment. For this embodiment, the tunable light source 110 is implemented with a tunable laser 210. For this embodiment, a free space beam of electro-magnetic radiation, emitted by the continuous wave, wavelength-tunable laser 210 impacts lens 1 (251) which collimates the beam of electro-magnetic radiation. The collimated beam of electro-magnetic radiation travels to a first fiber collimator (FiberPort) 256. The beam of electro-magnetic radiation then passes through a fiber isolator 255. The beam of electro-magnetic radiation then passes through a second fiber collimator (FiberPort) 257 that transforms the beam of electro-magnetic radiation, once again into a free-space beam of electro-magnetic radiation.

For at least some embodiments, the fiber isolator 255 serves two purposes, (1) to help suppress all but the desired mode or modes (TEMOO Transverse Electro-magnetic Mode, and (2) to isolate the laser source from back reflections that might be generated from optical components.

For at least some embodiments, the free-space beam of electro-magnetic radiation emitted from the second fiber collimator (FiberPort) 257 then impacts lens #2 (252) and lens #3 (253) and passes through beam steering mirrors 254.

As shown in FIG. 3, for an embodiment, the optical cavity 220 includes a cavity entrance mirror 223 and two cavity mirrors 221, 222. After passing through the beam steering mirrors 254, the electro-magnetic radiation then enters the three-mirror optical cavity 220 through the partially reflecting optical cavity entrance mirror 223. As shown, the optical cavity 220 includes an arrangement of mirrors 221, 222, 223 that forms a standing wave cavity. For an embodiment the optical cavity can be configured as a traveling wave cavity.

Figure 4:
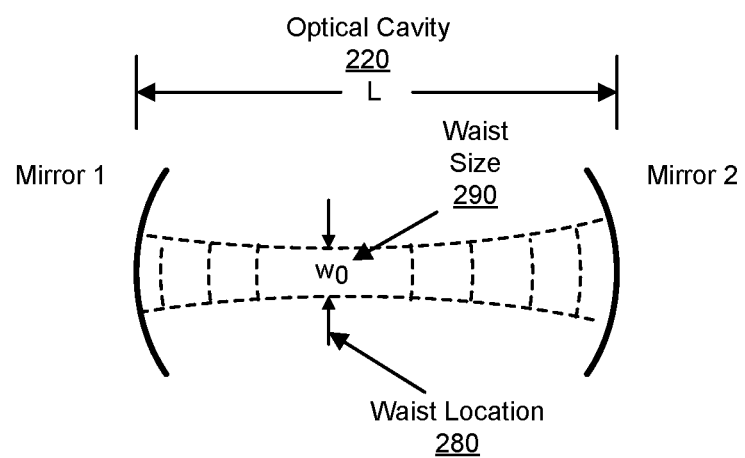
FIG. 4 is a block diagram that includes mode matching a beam of electro-magnetic radiation to an optical cavity, wherein a waist size and a waist location beam of electro-magnetic radiation matches a waist size and waist location defined by a physical design of the optical cavity.

FIG. 4 is a block diagram that includes mode matching a beam of electro-magnetic radiation to an optical cavity, wherein a waist size and a waist location of the beam of electro-magnetic radiation matches a waist size and waist location defined by a physical design of the optical cavity. While the cavity design of FIG. 4 includes only two mirrors (mirror1, mirror2), the descriptions are applicable to the three-mirror cavity of FIG. 3. The incoming beam of electro-magnetic radiation is considered mode matched to the optical cavity 220 when the incoming beam of electro-magnetic radiation's waist size and waist location matches that defined by the physical design of the optical cavity 220. The waist size 290 of electro-magnetic radiation is defined as the physical size of the electro-magnetic field pattern of radiation measured in a reference plane perpendicular (i.e., transverse) to the propagation direction of the electro-magnetic radiation. The waist location 280 of electro-magnetic radiation is defined as the physical location of the waist. When the waist size 290 or waist location 280 of the incoming beam of electro-magnetic radiation, is not mode matched by that defined by the optical cavity, a subset of the plurality of allowed axial-plus-transverse electro-magnetic radiation modes in the cavity which is greater than one can be excited.

The incoming beam of electro-magnetic radiation is considered aligned with the cavity when the incoming beam is steered into the optical cavity 220 such that the incoming beam of electro-magnetic radiation is congruent with the optical cavity axis. When the incoming beam of electro-magnetic radiation differs (not congruent or misaligned) with the cavity axis, a subset of the plurality of allowed axial-plus-transverse electromagnetic radiation modes in the cavity which is greater than one can be excited.

For an embodiment, the incoming beam of electro-magnetic radiation includes one or more transverse modes. When the incoming beam of electro-magnetic radiation includes more than one transverse mode, a subset of the plurality of allowed axial-plus-transverse electromagnetic radiation modes in the cavity which is greater than one can be excited.

Referring back to FIG. 3, for at least some embodiments, the lens #2 (252) and lens #3 (253) act as a telescope that matches the waist size and waist location of the incoming beam to that defined by the design of the optical cavity 220. For at least some embodiments, by changing the position of lens #2 and lens #3 along the direction of the electro-magnetic radiation, the waist size and/or waist location can be mode mismatched to that defined by the cavity.

In an embodiment, the incoming beam of electro-magnetic radiation includes one transverse mode. The beam is aligned with the optical axis of the cavity. A waist size and/or waist location of the incoming beam of electro-magnetic radiation is selected to be a different (not mode matched) from that defined by the physical design of the optical cavity 220 thereby exciting a subset of the plurality of allowed axial-plus-transverse electro-magnetic radiation modes in the cavity which is greater than one.

In an embodiment, the incoming beam of electro-magnetic radiation is described as one transverse electro-magnetic mode, a waist size and/or waist location of the incoming beam of electromagnetic radiation is selected to be the same as that defined by the physical design of the optical cavity 220. The beam is steered into the optical cavity 220 so that the incoming beam of electro-magnetic radiation is misaligned with the optical cavity axis thereby exciting a subset, which is greater than one, of the plurality of the allowed axial-plus-transverse electro-magnetic radiation modes. In an embodiment, this misalignment is implemented using two beam steering mirrors 254 to steer the electro-magnetic radiation into the optical cavity 220 such that a misalignment is created by introducing a displacement between the incoming beam of electro-magnetic radiation and the optical cavity axis of the optical cavity 220 thereby resulting in a beam of electro-magnetic radiation within the optical cavity 220 that excites only a subset of the plurality of allowed axial-plus-transverse electro-magnetic radiation modes which is greater than one. One method to displace the incoming beam of electro-magnetic radiation is to use the two steering mirrors 254 to tilt the incoming beam of electro-magnetic radiation so that it is misaligned with the optical cavity axis thereby exciting a subset, which is greater than one, of the plurality of the allowed axial-plus-transverse electro-magnetic radiation modes.

In another embodiment, the incoming beam of electro-magnetic radiation includes more than one transverse mode (s), thereby exciting a subset of the plurality of allowed axial-plus-transverse electro-magnetic radiation modes in the cavity which is greater than one.

In another embodiment, the incoming beam of electro-magnetic radiation includes more than one transverse mode(s). The incoming beam of electro-magnetic radiation is aligned with the cavity axis. A waist size and/or waist location of the incoming beam of electro-magnetic radiation is selected to be a different size than that defined by the physical design of the optical cavity 220 thereby exciting a subset of the plurality of allowed axial-plus-transverse electro-magnetic radiation modes in the cavity which is greater than one.

In another embodiment, the incoming beam of electro-magnetic radiation comprises more than one transverse mode. A waist size and/or waist location of the incoming beam of electromagnetic radiation is selected to be the same as that defined by the physical design of the optical cavity 220. The incoming beam of electro-magnetic radiation is misaligned with the optical axis of the cavity, thereby exciting a subset of the plurality of allowed axial-plus-transverse electro-magnetic radiation modes in the cavity which is greater than one.

In addition to the previously mentioned embodiments utilizing a single tunable light source to generate more than one transverse mode in the cavity, there are at least two other methods to generate more than one transverse modes in the cavity. One embodiment includes a light source that generates multiple transverse modes, and another embodiment includes using multiple light sources.

For at least some embodiments, the cavity detector 230 is placed such that the cavity detector 230 senses electro-magnetic radiation emanating from the optical cavity 220. The cavity detector 230 receives electro-magnetic radiation exiting the optical cavity 220 and produces a voltage or current that is proportional to the electro-magnetic radiation sensed by the cavity detector 230. The electro-magnetic radiation sensed by the cavity detector 230 is representative of the electro-magnetic radiation intensity inside the optical cavity 220, and for at least some embodiments, it is this electro-magnetic radiation that represents the electro-magnetic intensity, amplitude, a phase, or an amplitude and phase at a plurality of wavelengths.

For at least one embodiment, the cavity detector 230 generates data (sensed) in an analog form. For at least some embodiments, for input into and processing by the processor 240, the analog data is converted into digital form by and ADC (analog to digital converter) 291. The processor 240 records the received output at the plurality of wavelengths and detects the substance. For an embodiment the substance is detected based on the intensity, amplitude, a phase, or an amplitude and phase of the sensed electro-magnetic radiation emanating from the optical cavity 220 at one or more of the plurality of wavelengths while the optical cavity 220 receives the beam of electro-magnetic radiation.

For at least some embodiments, the incoming beam of electro-magnetic radiation can be described or represented by a linear combination of transverse modes. The transverse mode of electro-magnetic radiation is defined as a particular (transverse) electro-magnetic field pattern of radiation measured in a plane perpendicular (i.e., transverse) to the propagation direction of the electro-magnetic radiation. If a transverse wave is moving in the z direction, its oscillations lie in the x-y plane, and the Electric field oscillates in one plane, for instance the x plane, while the Magnetic field oscillates in the perpendicular plane, for instance the y plane.

Figure 5:
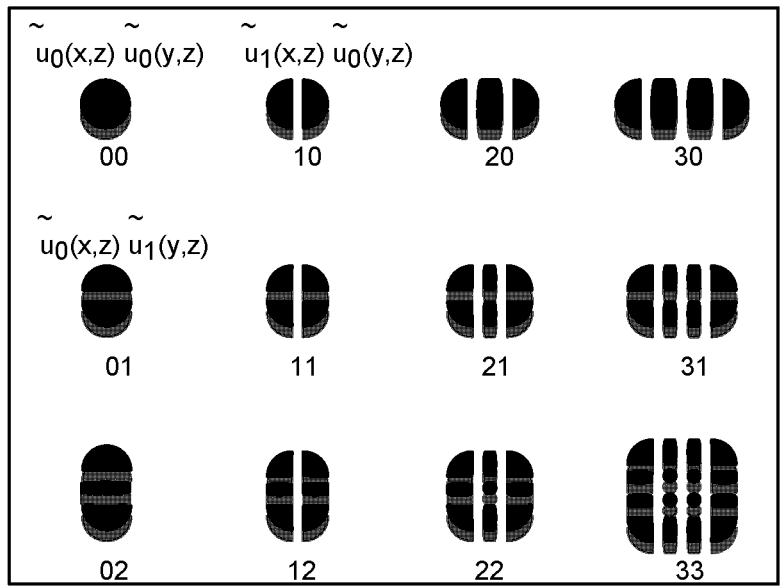
FIG. 5 shows examples of Hermite-Gaussian transverse modes, according to an embodiment.

FIG. 5 shows examples of Hermite-Gaussian transverse modes, according to an embodiment. Specifically, FIG. 5 shows examples of transverse modes for a beam of light, such as the light generated by a laser. The dark areas represent the concentration of intensity in the cross-section slice of the wave propagating in the medium (free space or optical cavity) on the z-plane.

The term $\tilde{u}_0(x,z)\tilde{u}_0(y,z)$ is referred to as the lowest-order Gaussian mode (TEM 00) and its transverse component can be described as a round "slab" or disk. The function $\tilde{u}_1(x,z)\tilde{u}_0(y,z)$ is called the first-order Gaussian mode in x and the lowest-order mode in y and as can be seen in FIG. 5 has two lobes along the x dimension. The function $\tilde{u}_0(x,z)\tilde{u}_1(y,z)$ is called the first-order Gaussian mode in y and the lowest-order mode in x and as can be seen in FIG. 5 the beam has two lobs alone the y dimension. For higher order modes, the same logic can be used. These Gaussian modes can, under specific conditions, be used to describe a beam of electro-magnetic radiation travelling in free-space or in an optical cavity.

A beam of Electro-magnetic radiation in an optical cavity (such as, optical cavity 220) can also be described using axial-plus-transverse modes that are allowed. Allowed cavity modes (allowed axial-plus-transverse electro-magnetic radiation modes) can be understood using a framework in the wavelength domain.

When resonator theory is applied to an arrangement of 2 or more mirrors forming an optical cavity, the steady-state resonance condition becomes, $$r_1 r_2 r_3 \ldots r_n e^{-j\frac{\omega \rho}{c}} = 1$$

where the coefficients $r_1$, $r_2$, $r_3$, . . . $r_n$, are the wave-amplitude reflection coefficients for mirror 1, mirror 2, mirror 3, . . . mirror n which defines the cavity; $\omega$ is the angular frequency of the optical wave, $\lambda$ is the wavelength of the optical wave, c is the speed of electro-magnetic radiation, $$e^{-j\frac{\omega \rho}{c}} = 1$$

is the phase shift for one full trip around the optical cavity with a round-trip distance designated as p, and $\psi_{nm}$, is the "Guoy phase shift" phase angle. The resonance condition equation expresses the round-trip phase shift conditions under which the system oscillates with greater electro-magnetic amplitudes than when the resonance condition is not met. The greater amplitudes produced while meeting this resonance condition is called allowed axial-plus-transverse modes. FIG. 5 shows an example of allowed axial-plus-transverse modes. The "allowed" axial-plus-transverse modes in the optical cavity are those where the cavity round-trip distance is equal to an integer number of wavelengths.

Allowed axial-plus-transverse modes can occur at a plurality of wavelengths. Axial-plus-transverse modes in an optical cavity can be described mathematically in the following manor. The electro-magnetic amplitude in an optical cavity can be described in Cartesian coordinates using the paraxial wave equation:

$$\left(\frac{\partial^2}{\partial x^2} + \frac{\partial^2}{\partial y^2} + 2jk\frac{\partial}{\partial z}\right)\tilde{E}(x, y, z) = 0$$

where $\tilde{E}(x, y, z)=0$ is the electro-magnetic amplitude in the cavity.

The "Guoy phase shift" is associated with the fact that different axial-plus-transverse modes can accumulate phase at different rates. If one identifies the axial-plus-transverse modes of a given optical cavity, one can also find the exact angular frequencies (wavelengths) at which the resonance condition is met. The resonance angular frequencies, including the Guoy phase shift, of the Hermite-Gaussian axial-plus-transverse modes for a two mirror cavity made up of mirrors $M_1$ and $M_2$ are given by a plurality of wavelengths described by:

$$\omega = \omega_{qnm} = \left[q + (n+m+1)\frac{\cos^{-1}\left(\pm\sqrt{g_1 g_2}\right)}{\pi}\right] \times \frac{2\pi c}{p}$$

where p is the round-trip path length in the optical cavity, c is the speed of electro-magnetic radiation, and where the parameters "g" are given by;

$$g_1 \equiv 1 - \frac{L}{R_1} \quad g_2 \equiv 1 - \frac{L}{R_2}$$

where the parameters $R_1$ and $R_2$ are the radius of curvatures of mirror $M_1$ and $M_2$, respectively. The resonance angular frequencies are degenerate with respect to the indices n and m through the (n+m+1) term.

In cylindrical coordinates, the resonance angular frequencies of the Laguerre-Gaussian axial-plus-transverse modes in the optical cavity are then given by a plurality of wavelengths described by, $$\omega = \omega_{qpl} = \left[q + (|l|+2p+1)\frac{\cos^{-1}\left(\pm\sqrt{g_1 g_2}\right)}{\pi}\right] \times \left(\frac{2\pi c}{p}\right)$$

In this case, the resonance angular frequencies are degenerate with respect to the indices l and p through the (|l|2p+1) term.

In an embodiment, electro-magnetic amplitudes at a plurality of wavelengths can be excited using two beam steering mirrors to create a mode mismatch between the incoming beam of electro-magnetic radiation and the optical cavity. The number of allowed axial-plus-transverse electro-magnetic radiation modes excited is related to the amount of misalignment between the incoming beam of electro-magnetic radiation and the optical cavity axis. The electro-magnetic amplitude of the axial-plus-transverse modes is related to the amount of misalignment between the incoming beam of electro-magnetic radiation and the optical cavity axis.

In mathematical terms, in the case where the optical cavity has losses, the angular frequencies, which make up optical cavity modes cannot be completely described as delta functions. With optical loss, the electro-magnetic radiation in the optical cavity can be described as a superposition of a large number of waves, separated by equal phase shifts but with amplitudes that are geometrically reduced by loss in the optical cavity. Because of this geometric term, the higher the optical cavity loss translates to a wider axial-plus-transverse cavity mode in the frequency domain. When considering a plurality of axial-plus-transverse modes, overlapping frequencies of two or more modes can cause transverse mode beating which will introduce large intensity variations, as a function of time, in each undistinguished axial-plus-transverse mode. This inter-modulation distortion will result in a noisier measurement thereby degrading system signal-to-noise ratio and sensitivity. As an example, suppose an optical cavity is oscillating simultaneously in two indistinguishable modes in the frequency domain. The indices of these modes is $q_1 n_1 m_1$ and $q_2 n_2 m_2$. The total output power from the cavity associated with these two indistinguishable modes can be written as;

$$i(t) = I_{01} + I_{02} + I_{12}\cos[(\omega_2 - \omega_1)t + \phi_{12}]$$

where $I_{01}$ and $I_{02}$ are the dc intensities due to each separate mode, plus a cross product or beat frequency term $I_{12}\cos[(\omega_2-\omega_1)t+\phi_{12}]$ between the two signals. If both modes have the exact same frequency, as in the degenerative case, then $(\omega_2\omega_1)=0$ and there is no time dependence on i(t). However, if $(\omega_2-\omega_1)\neq 0$, then there will be a time dependent variation of the total intensity, i (t) with a period defined by the frequency separation of the two modes. This time dependent variation would introduce unwanted noise on the intensity measurement thereby impacting performance. The axial-plus-transverse modes excited is a subset of the allowed axial-plus-transverse optical cavity modes that, except in the degenerative case, do not overlap in the frequency domain and/or do not produce mode beating (mixing products) and/or minimize mode beating in the frequency domain.

Laser Tuning

As previously described, for an embodiment, the laser generates a beam of electro-magnetic radiation, wherein a wavelength of the beam of electro-magnetic radiation is tuned to operate at a plurality of wavelengths. For at least some embodiments, each axial-plus-transverse optical cavity mode is excited when electro-magnetic radiation entering the optical cavity 220 meets the resonance conditions of the optical cavity, including excitation wavelength.

Figure 6:
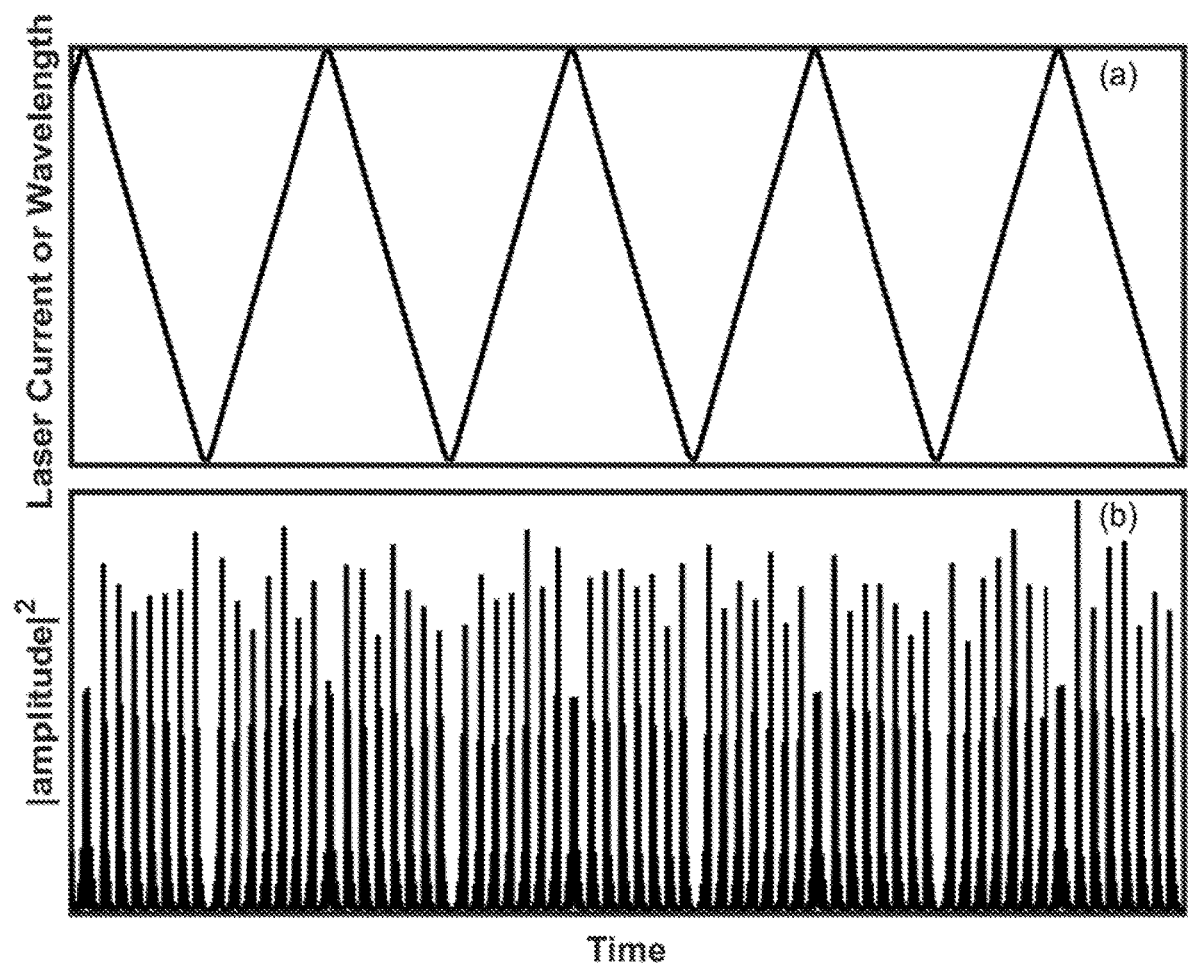
FIG. 6 shows an example of a triangle waveform being used to tune a wavelength of the laser, according to an embodiment.

At least some embodiments include continuous Laser Current and/or Temperature Tuning. Specifically, in an embodiment, the laser current and/or laser temperature is varied over a range of currents and/or temperatures thus causing the laser to radiate electro-magnetic energy over a range of different wavelengths (frequencies). For an embodiment, these variations in current and/or temperature are periodic and can be described using linear (such as a triangle wave in FIG. 6), sinusoidal or non-sinusoidal waveforms; resulting in variations in the laser wavelength. By varying the wavelength, a plurality of axial-plus-transverse electro-magnetic radiation modes is excited. FIG. 6 shows an example of a triangle waveform being used to tune a wavelength of the laser, according to an embodiment. That is, FIG. 6 shows an example of greater and lesser electro-magnetic intensities at a plurality of wavelengths while varying the laser wavelength using a triangle waveform.

Figure 7:
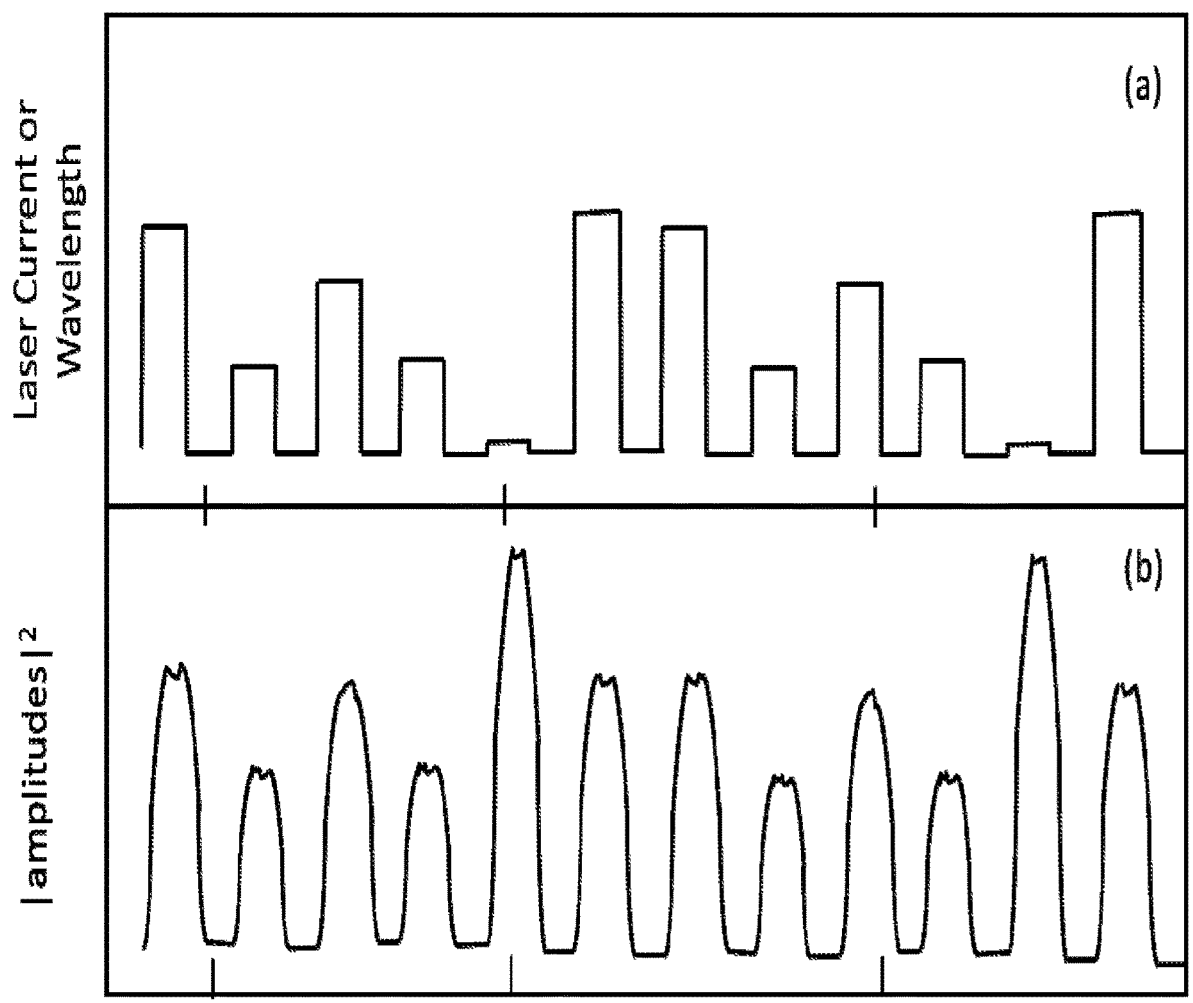
FIG. 7 shows an example of discrete steps being used to change the wavelength of the laser, according to an embodiment.

At least some embodiments include discrete laser current tuning. Specifically, in an embodiment, the laser current is varied using a sequence of current steps. These discrete steps in current result in discrete steps in the laser wavelength. By stepping the laser wavelength, a plurality of axial-plus-transverse electro-magnetic radiation modes is activated. FIG. 7 shows an example of discrete steps being used to change the wavelength of the laser, according to an embodiment. Specifically, FIG. 7 shows an example of greater and lesser electro-magnetic intensities while varying the laser wavelength using discrete steps.

Figure 8:
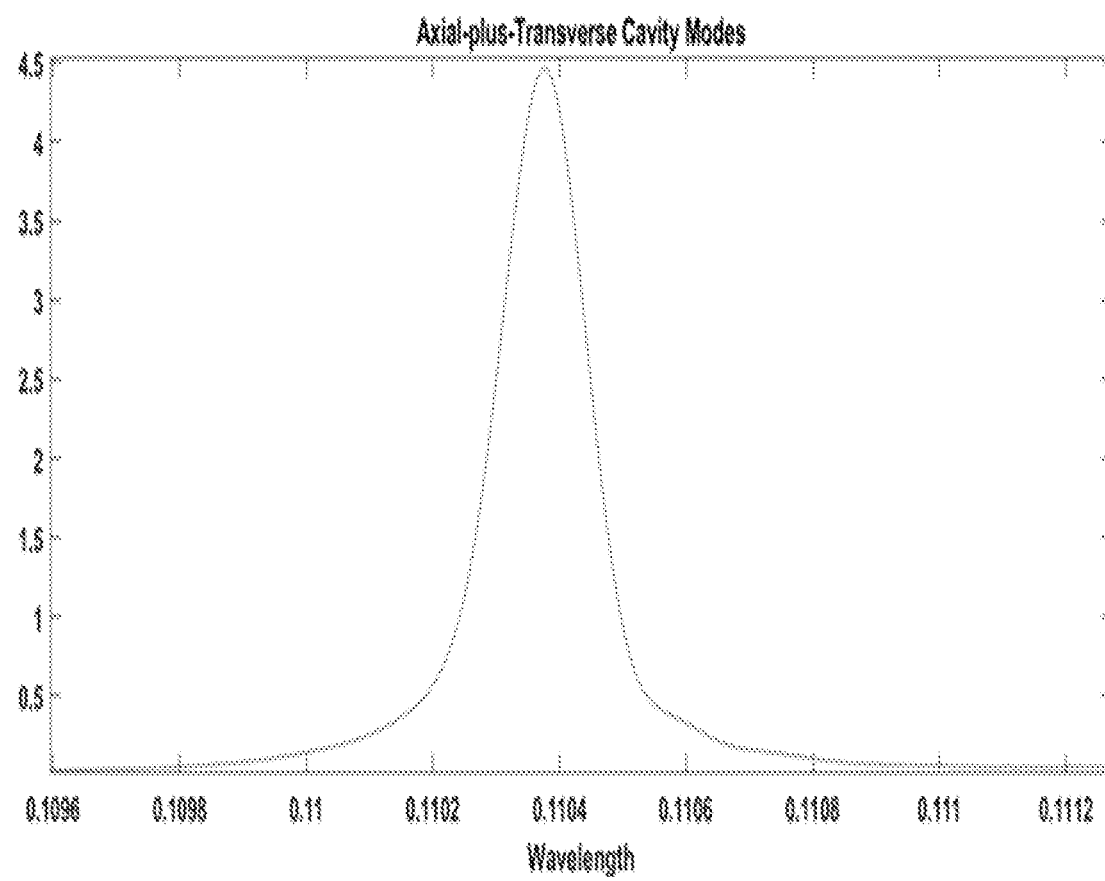
FIG. 8 shows an example of summing areas under each axial-plus-transverse mode, according to an embodiment.

For at least some embodiments, detecting the substance is based on a variation in a shape of an intensity, an amplitude, a phase, or an amplitude and phase of axial-plus-transverse electro-magnetic modes of the sensed electro-magnetic radiation. When optical loss is introduced, axial-plus-transverse electro-magnetic radiation modes no longer resonate at a single frequency. FIG. 8 shows an example of summing areas under each axial-plus-transverse mode, according to an embodiment. Specifically, FIG. 8 shows each axial-plus-transverse electro-magnetic radiation mode has intensity variation in the frequency domain. In an embodiment, integrating over the excited intensity at a plurality of wavelengths provides information about optical cavity loss.

Figure 9:
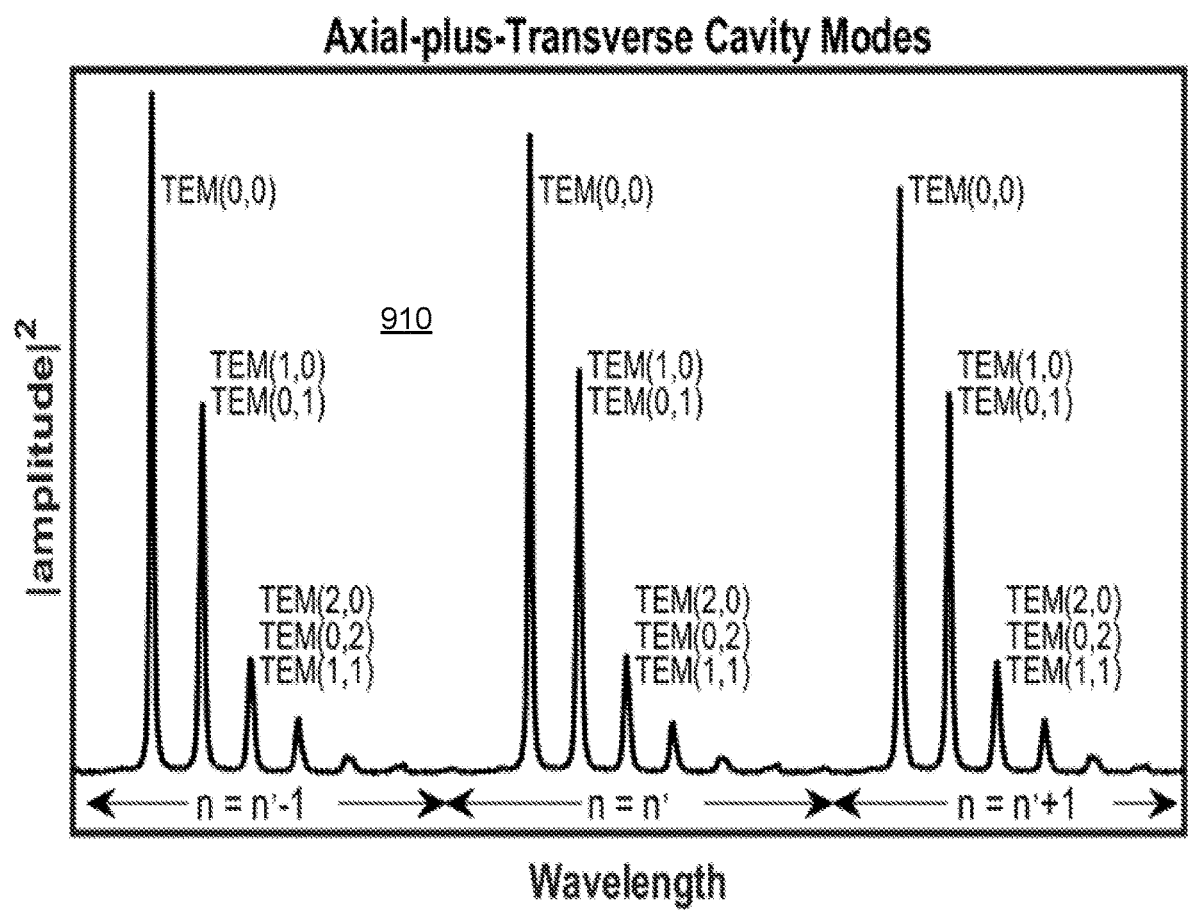
FIG. 9 shows a plot that depicts an example of axial modes, each containing multiple transverse modes, according to an embodiment.

Hermite-Gaussian modes can be used to describe the electro-magnetic amplitudes in the cavity. FIG. 9 shows a plot 910 that depict an example of axial modes, each containing multiple transverse modes, according to an embodiment. Specifically, the plot 910 of FIG. 9 shows an example of a plurality of Hermite-Gaussian axial-plus-transverse electro-magnetic radiation modes. In this example, three sets of axial modes, q, each containing multiple transverse modes, have been excited. Each mode is designated as $TEM_{nm}$, where the integer n is the x-coordinate index and the integer m is the y-coordinate index. By comparing intensities at the plurality of wavelengths with theory, axial-plus-transverse electro-magnetic radiation modes can be identified and the peak intensity for each can be determined.

In an embodiment, the laser wavelength is varied to activate a plurality of allowed axial-plus-transverse electro-magnetic radiation modes and at least one of an intensity, an amplitude, a phase, or an amplitude and phase of the sensed electro-magnetic radiation emanating from the optical cavity are detected. The repetitive pattern can be used to uniquely identify each mode and associate the measured electro-magnetic radiation to each axial-plus-transverse mode.

In another embodiment, the laser wavelength is varied to activate a plurality of allowed axial-plus-transverse electro-magnetic radiation modes and at least one of an intensity, an amplitude, a phase, or an amplitude and phase of the sensed electro-magnetic radiation emanating from the optical cavity are detected. The amplitude of the laser tuning voltage can be used to uniquely identify each mode and associate the measured electro-magnetic radiation to each axial-plus-transverse optical cavity mode.

Figure 10:
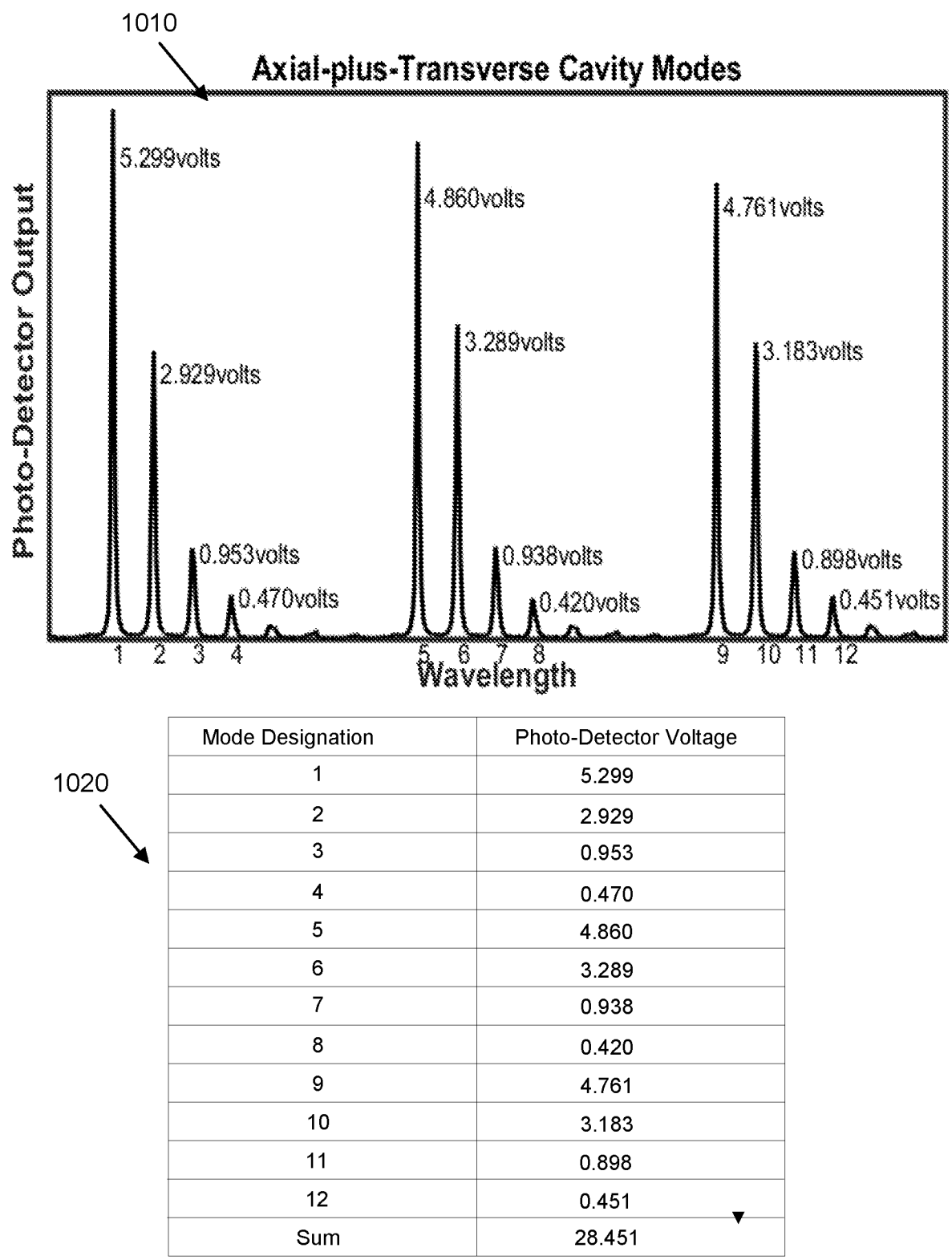
FIG. 10 shows a plot and a table that depict an example of summing peak amplitude measurements of axial-plus-transverse modes made with a cavity-detector, according to an embodiment.

For at least some embodiments, detecting the substance includes summing at least one of an intensity, an amplitude, a phase, or an amplitude and phase of allowed axial-plus-transverse electro-magnetic modes of the sensed electro-magnetic radiation. Because the electro-magnetic radiation in an optical cavity is governed by optical losses and wherein the cavity detector senses electro-magnetic radiation emanating from the optical cavity, the cavity detector can provide a measurement of optical loss in the cavity, at least one of an intensity, an amplitude, a phase, or an amplitude and phase of each excited axial-plus-transverse electro-magnetic radiation mode can be measured. For example, by summing the peaks intensities of identified axial-plus-transverse optical cavity modes over a plurality of wavelengths, information about optical cavity loss can be obtained. FIG. 10 shows a plot 1010 and a table 1020 that depict an example of summing peak amplitude measurements of axial-plus-transverse modes made with a cavity-detector, according to an embodiment. For at least some embodiments, the summation includes one or more of the measured excited allowed axial-plus-transverse optical cavity modes.

Figure 11:
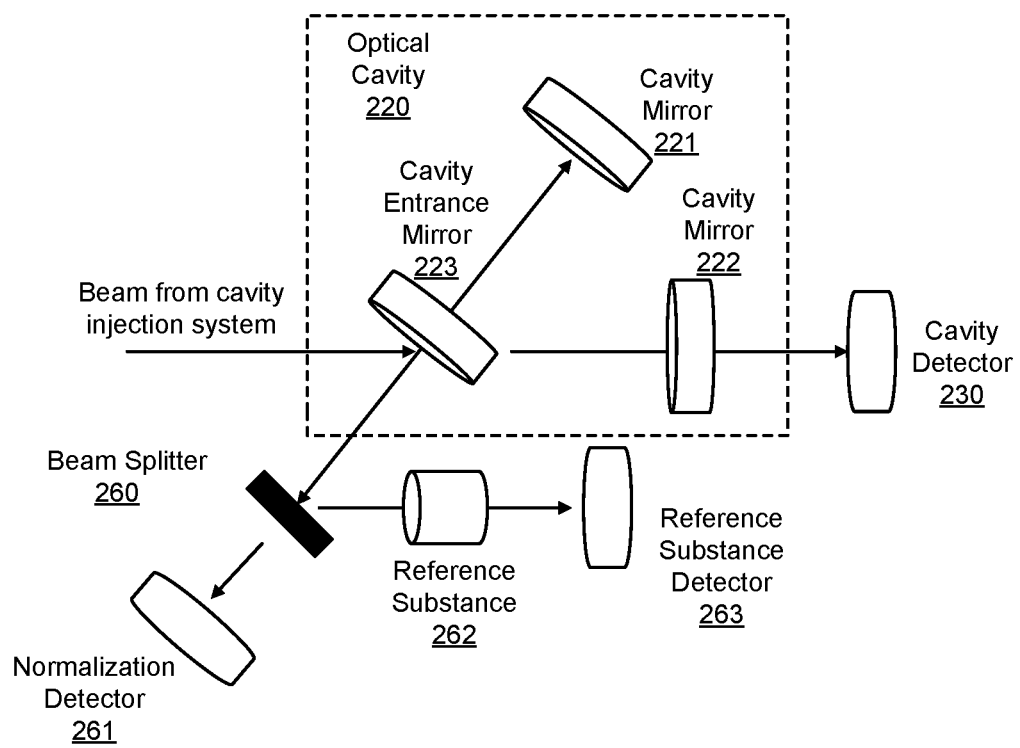
FIG. 11 shows an example of a block diagram that includes a reference substance and beam normalization, according to an embodiment.

At least some embodiments further include a second normalization detector (such as, normalization detector 261) sensing electro-magnetic radiation reflected off an entrance to the optical cavity, wherein the processor further operates to monitor the sensed electro-magnetic radiation reflected off the entrance to the optical cavity. In order to represent the electro-magnetic radiation intensity entering the optical cavity, the beam reflected from the entrance to the optical cavity can be monitored. FIG. 11 shows an example of a block diagram that includes a reference substance detector 263 and normalization detector 261, according to an embodiment. In this embodiment, electro-magnetic radiation from the laser (beam from cavity injection system) is directed into the optical cavity 220. A portion of that electro-magnetic radiation passes through the partially reflecting cavity entrance mirror 223 while another portion is reflected off the cavity entrance mirror 223. The electro-magnetic radiation reflected off the cavity entrance mirror 223 is transported to the partially reflecting beam splitter 260. At the beam splitter 260 a portion of the electro-magnetic radiation is transmitted through the beam splitter 260 and sensed by the photo detector, such as, the normalization detector 261. A beam normalization measurement of the normalization detector 261 must be made at wavelengths where the optical cavity 220 is not in resonance. When the optical cavity 220 is not in resonance, the electro-magnetic radiation sensed by the normalization detector 261 is proportional to the electro-magnetic radiation entering the optical cavity 220.

For at least some embodiments, the processor 240 further operates to account for effects of electro-magnetic radiation changes emanating from the optical cavity 220 caused by changes in an intensity, amplitude, phase, or amplitude and phase of the electro-magnetic radiation entering the optical cavity 220 including measuring the intensity, amplitude, phase, or amplitude and phase of the sensed electro-magnetic radiation reflected off the entrance to the optical cavity 220 and correcting the electro-magnetic radiation emanating from the cavity based on the intensity, amplitude, phase, or amplitude and phase measured by the normalization detector 261.

Figure 12:
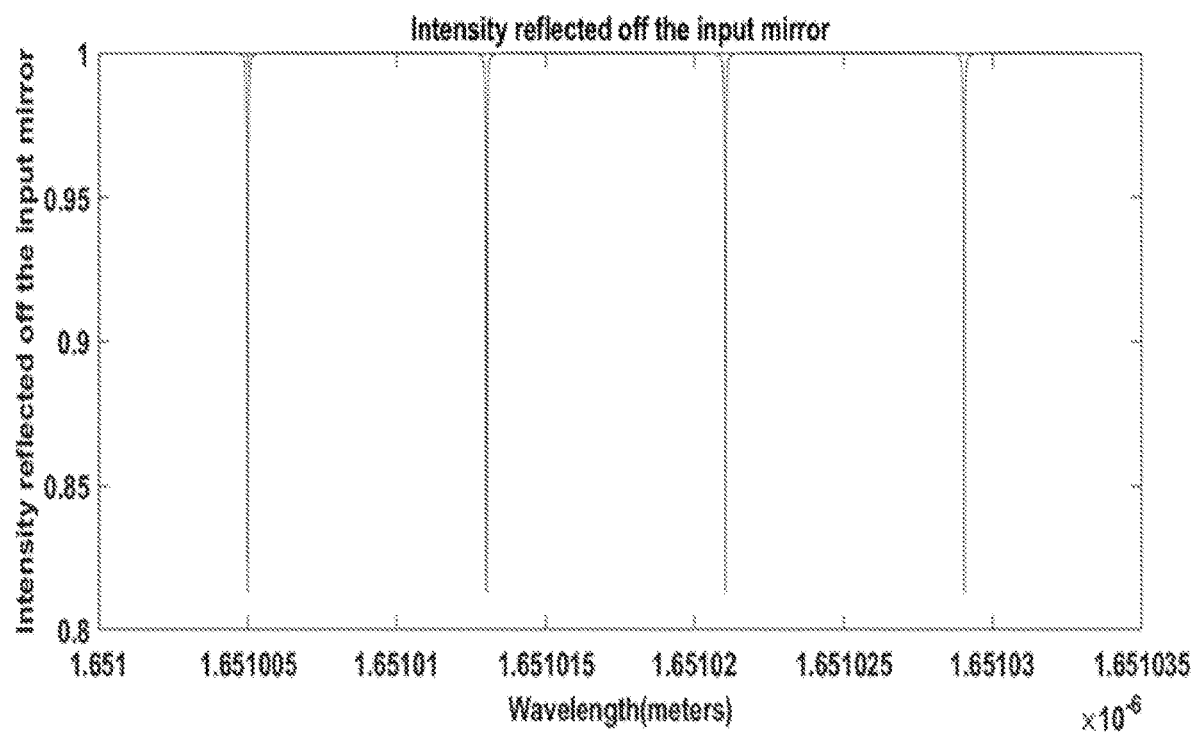
FIG. 12 shows a calculated intensity as sensed by a normalization detector, according to an embodiment.

FIG. 12 shows a calculation of the intensity as sensed by the normalization detector 261, according to an embodiment. Specifically, in this embodiment the electro-magnetic radiation reflected off the optical cavity entrance mirror is monitored using the normalization detector 261 while varying the laser wavelength. As the laser frequency is altered the optical cavity goes into and out of optical cavity resonances repeating the pattern for each free-spectral range of the optical cavity. When off resonance, the intensity of the electro-magnetic radiation on the normalization detector 261 is proportional to the beam intensity entering the cavity and as such is a monitor signal for the light intensity entering the optical cavity 220.

In an embodiment, by comparing the output of the cavity detector with the output of the normalization detector 261, corrections for electro-magnetic radiation changes emanating from the optical cavity 220 caused by changes in the intensity of the electro-magnetic radiation entering the optical cavity 220 can be made.

For at least some embodiments, the processor further operates to tune the wavelength of the beam of electro-magnetic radiation based on monitoring electro-magnetic radiation exiting from a reference substance, wherein at least a portion of the electro-magnetic radiation reflected off the entrance to the optical cavity is passed through the reference substance, and wherein the reference substance is selected to insure that a frequency of the electro-magnetic radiation corresponds to a frequency at which an absorption of the substance is measured.

In an embodiment, the beam of electro-magnetic radiation from the laser enters the optical cavity 220 through the partially reflecting optical cavity entrance mirror 223. A portion of that electro-magnetic radiation passes through the partially reflecting optical cavity entrance mirror 223 while another portion is reflected off the mirror 223. The electro-magnetic radiation reflected off the cavity entrance mirror 223 is transported to the partially reflecting beam splitter 260. At this beam splitter 260 a portion of the electro-magnetic radiation is reflected off the beam splitter 260 and is directed through the reference substance 262 and sensed by the reference substance detector 263 as shown in FIGS. 3 and 11.

For an embodiment, the reference substance has enough reference species of interest to make an absorption measurement possible, and must have sufficient path length to make an absorption measurement.

Figure 13:
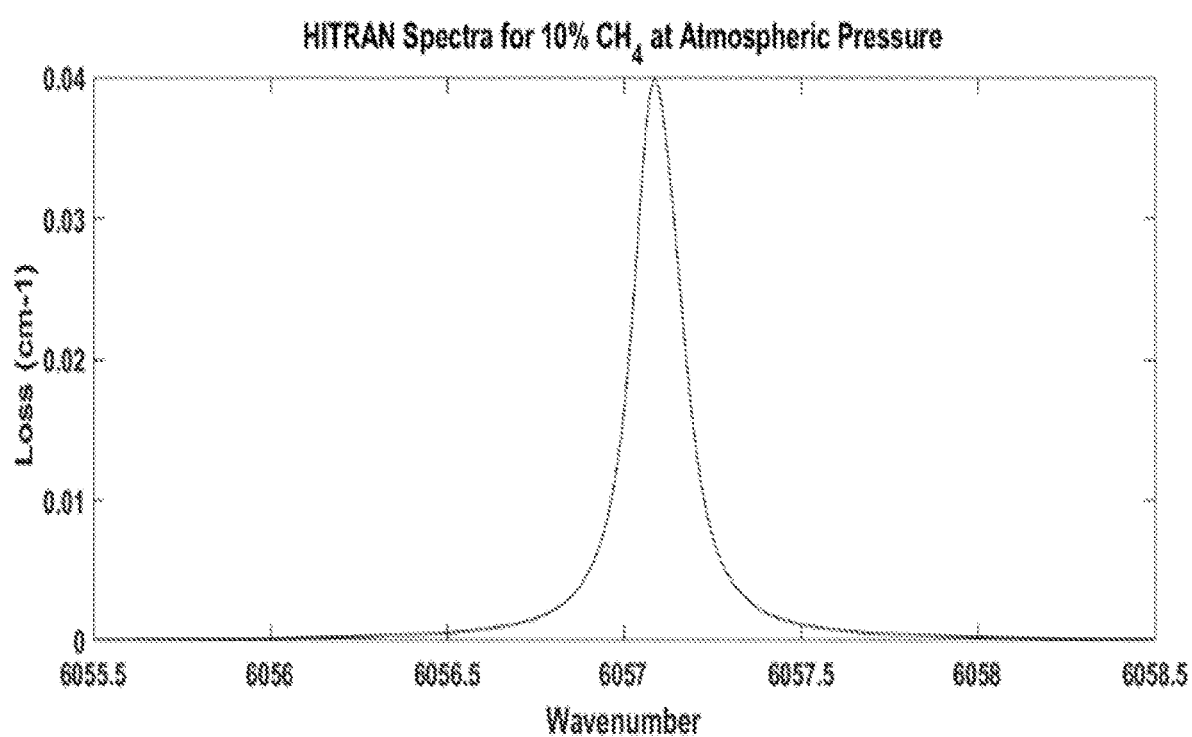
FIG. 13 shows an absorbance spectra for methane when measured at atmospheric pressure, according to an embodiment.

The processor 240 receives the information of the sensed electro-magnetic radiation from the Reference Substance detector 263 and further operates to tune the wavelength of the beam of electro-magnetic radiation by adjusting the laser ramp offset voltage such that the average laser ramp voltage corresponds to a wavelength consistence with the absorbance wavelength of the substance of interest. This ensures that the laser remains centered at the wavelength of the absorbance feature and as such centered on the absorbance of the substance of interest. FIG. 13 shows an absorbance spectra for methane when measured at atmospheric pressure, according to an embodiment.

For at least some embodiments, as in the case of a normalization determination, a valid reference substance determination requires that the measurement be made when the optical cavity 220 is not in resonance. For an embodiment, this requirement is, again, met by selecting laser frequencies where the optical cavity is not in resonances. For an embodiment, this is accomplished by monitoring the signal on the cavity detector 230 and selecting laser frequencies where no optical cavity resonances occur.

Figure 14:
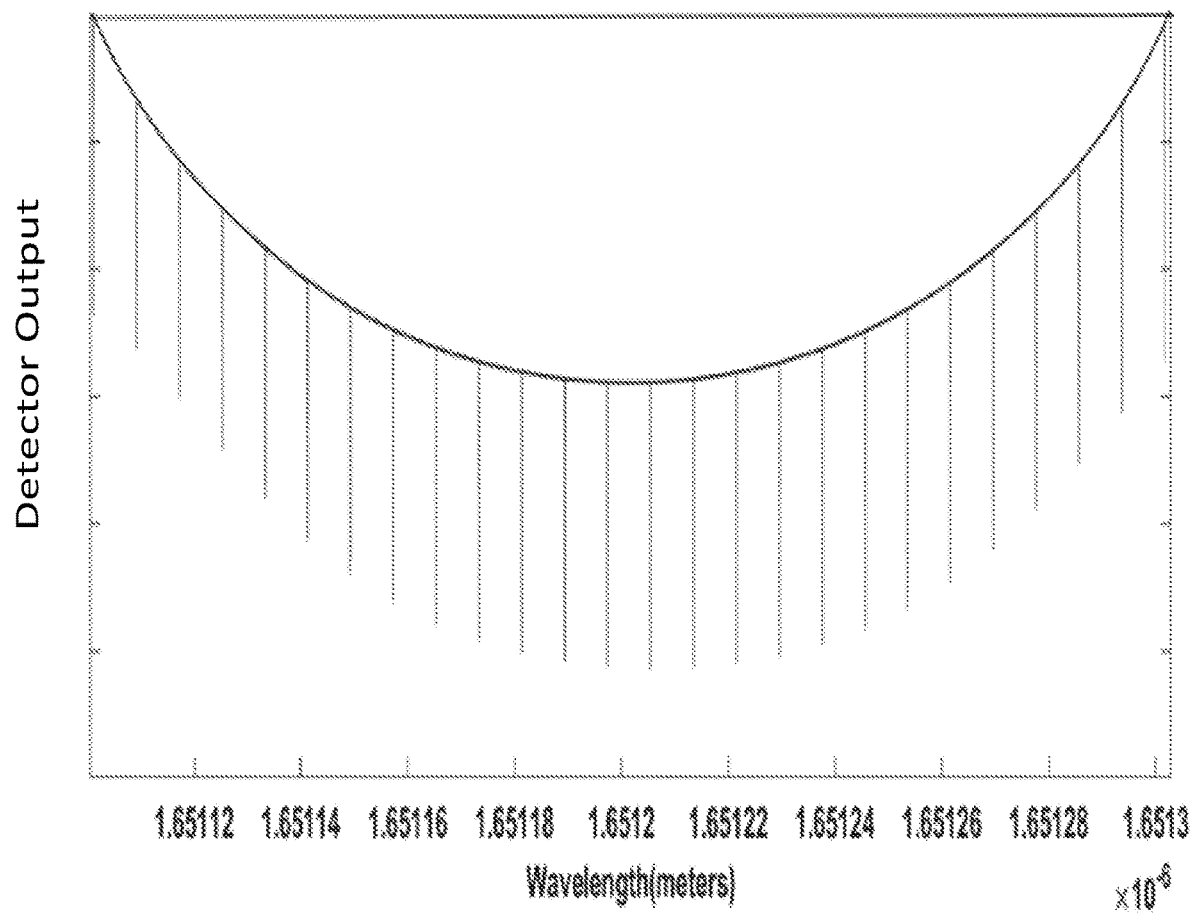
FIG. 14 shows an example of a reference cell detector signal when the average laser ramp voltage corresponds to the peak wavelength of the reference absorbance feature, according to an embodiment.

FIG. 14 shows an example of a reference cell detector signal when the average laser ramp voltage corresponds to the peak wavelength of the reference absorbance feature, according to an embodiment. Specifically, the calculated reference substance detector signal when the average laser ramp voltage corresponds to the peak wavelength of the methane absorbance feature is shown in FIG. 14.

For at least some embodiments, the processor further operates to tune the beam of electro-magnetic radiation over the plurality of wavelengths one or multiple times, and record the information related to the sensed electro-magnetic radiation at the plurality of wavelengths. For at least some embodiments, the processor further operates to sum the recorded information related to the sensed electro-magnetic radiation for each of the plurality of wavelengths over the one or multiple times. For at least some embodiments, the processor further operates to identify repetitive patterns in the recorded information related to the sensed electro-magnetic radiation for each of the plurality of wavelengths over the one or multiple times. For at least some embodiments, the processor further operates to detect an amount of the substance based on the identified repetitive patterns in the summed recorded information related to the sensed electro-magnetic radiation for each of the plurality of wavelengths over the one or multiple times.

More information regarding the optical loss can be obtained by tuning the laser to the same plurality of wavelengths multiple times. FIGS. 6 and 7 depict laser control system signals in which the processor 240 operates to repeatedly tune the beam of electro-magnetic radiation over the same plurality of wavelengths multiple times. For an embodiment, the processor 240 further operates to record intensity of the received output at the plurality of wavelengths at each of the plurality of wavelengths, each of the multiple times. For an embodiment, the processor 240 further operates to sum the recorded intensity for each of the plurality of wavelengths over the multiple times. For an embodiment, the processor further operates to identify repetitive patterns in the summed recorded intensity for each of the plurality of wavelengths over the multiple times. For an embodiment, the processor further operates to detect the amount of the substance based on the identified patterns in the summed recorded intensity for each of the plurality of wavelengths over the multiple times.

For an embodiment, the cavity includes an optical cavity 220 wherein the optical cavity 220 comprises 2 or more mirrors forming the optical cavity, wherein the optical cavity receives the beam of electro-magnetic radiation; wherein successive reflections of the electro-magnetic radiation at each of the 2 or more mirrors occurs at one common physical location on each mirror.

For an embodiment, the beam of electro-magnetic radiation is selected to ensure that one axial-plus-transverse electro-magnetic mode is dominate at any one of the plurality of wavelengths.

For at least some embodiments, the processor receives information from one or more detectors relating to a portion of the beam of electro-magnetic radiation not entering the cavity, wherein the detectors (261, 263) are arranged in a physical configuration such that the information they provide in conjunction with the sensed (sensed by cavity detector 260) electro-magnetic radiation emanating from the optical cavity increases the measurement range of the substance detectable, wherein the sensed signal in conjunction with the cavity detector increases the measurement range of the substance detectable. Specifically, information received from the cavity detector and information received from one or more detectors is used to detect the sub stance.

For an embodiment, the amount of the substance detected is limited by the cavity detector and processor's capability to measure excited allowed axial-plus-transverse electro-magnetic radiation modes when the majority of electro-magnetic radiation in the cavity is absorbed by the substance. Information from one or more detectors sensing electro-magnetic radiation not entering the cavity may be used to detect the substance when a substance absorbs the majority of electro-magnetic radiation in the cavity. Combining the information from the cavity detector and the information from one or more detectors sensing electro-magnetic radiation not entering the cavity may increase the measurement range of the substance detectable.

Referring back to FIG. 3, and as previously stated, at least some embodiments are configured to increase the amount of substance detected. The measurement range is limited by a number of factors such as the cavity saturation, cavity detector dynamic range and Analog-to-Digital converters. The goal of the cavity system is to enhance the substance detection at very low levels such as 1 to 1000 ppm. In order to extend the measurement range to higher values the detectors outside the cavity may be utilized.

The substance absorbs electro-magnetic radiation outside the cavity in the optical paths of a beam splitter 260 and a reference Substance 262. As shown, for an embodiment, the detectors are arranged in a physical configuration such that the propagation length of the path from the beam splitter 260 to the normalization detector 261 and the path from the Beam splitter 260 to the reference substance detector 263 is different; therefore the information from the normalization detector 261 and reference substance detector 263 can be used to determine the amount of the substance detected by measuring losses external to the cavity.

The cavity 220 improves measurement sensitivity by adding gain to the system to measure the substance at very low levels of concentration. In the absence of the cavity 220 the substance may be detected at higher levels of concentration. By combining the information derived from the cavity 220 and cavity detector 230 with information derived outside the cavity through the normalization detector 261 and reference substance detector 263 the concentration range of substance detected can be extended.

Figure 15:
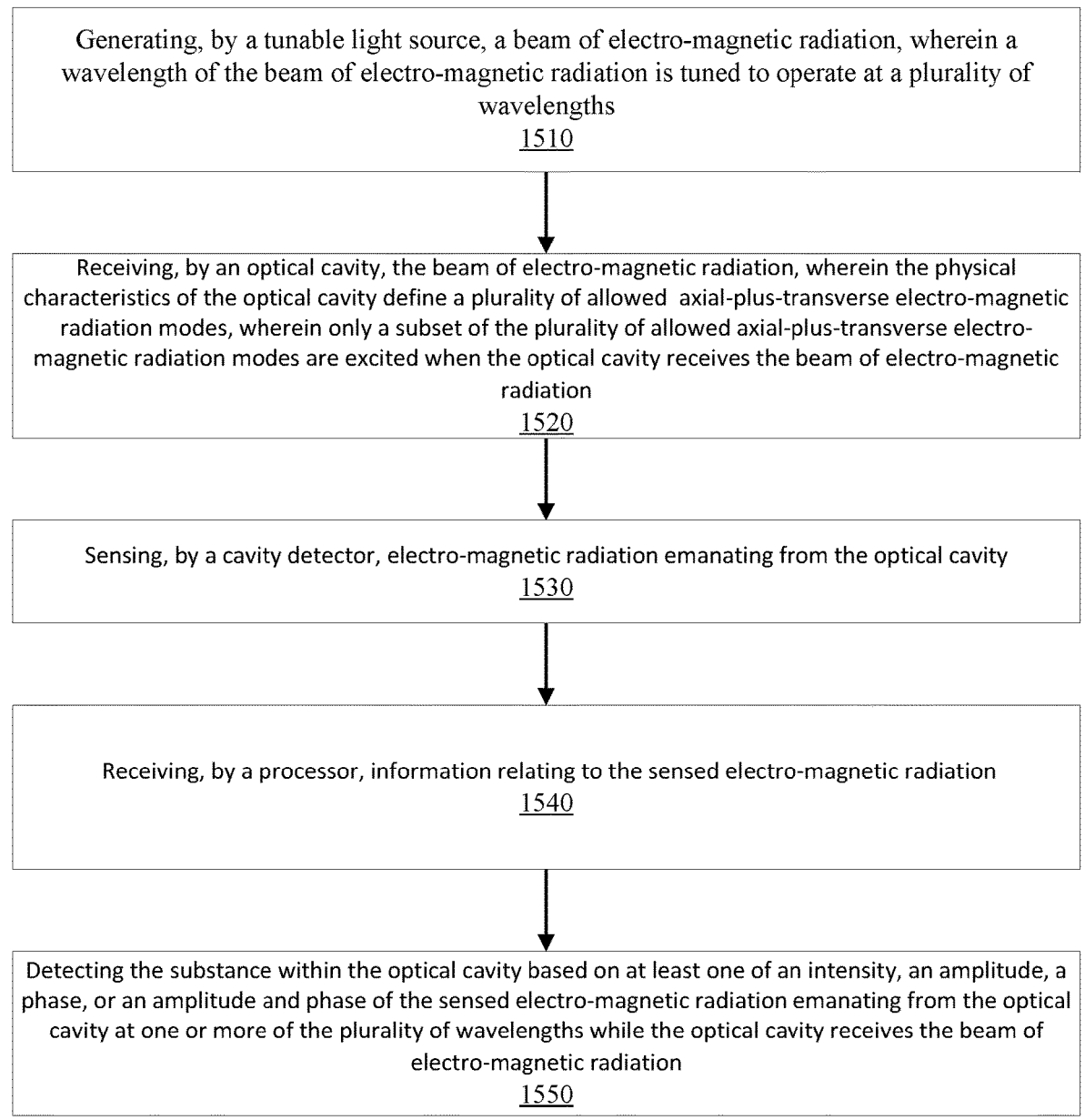
FIG. 15 is a flow chart that includes steps of a method to measure data, according to an embodiment.

FIG. 15 is a flow chart that includes steps of a method to measure data, according to an embodiment. A first step 1510 includes generating, by a tunable light source, a beam of electro-magnetic radiation, wherein a wavelength of the beam of electro-magnetic radiation is tuned to operate at a plurality of wavelengths. A second step 1520 includes receiving, by an optical cavity, the beam of electro-magnetic radiation, wherein the physical characteristics of the optical cavity define a plurality of allowed axial-plus-transverse electro-magnetic radiation modes, wherein only a subset of the plurality of allowed axial-plus-transverse electro-magnetic radiation modes are excited when the optical cavity receives the beam of electro-magnetic radiation. A third step 1530 includes sensing, by a cavity detector, electro-magnetic radiation emanating from the optical cavity. A fourth step 1540 includes receiving, by a processor, information relating to the sensed electro-magnetic radiation. A fifth step 1550 includes detecting the substance within the optical cavity based on at least one of an intensity, an amplitude, a phase, or an amplitude and phase of the sensed electro-magnetic radiation emanating from the optical cavity at one or more of the plurality of wavelengths while the optical cavity receives the beam of electro-magnetic radiation.

As previously described, for at least some embodiments, detecting the substance is based on a variation in a shape of an intensity, an amplitude, a phase, or an amplitude and phase of axial-plus-transverse electromagnetic modes of the sensed electro-magnetic radiation. As previously described, for at least some embodiments, detecting the substance comprises summing at least one of an intensity, an amplitude, a phase, or an amplitude and phase of axial-plus-transverse electromagnetic modes of the sensed electro-magnetic radiation.

As previously described, at least some embodiments include sensing, by a normalization detector, electro-magnetic radiation reflected off an entrance to the optical cavity, wherein the processor further operates to monitor the sensed electro-magnetic radiation reflected off the entrance to the optical cavity. As previously described, at least some embodiments include accounting for effects of electro-magnetic radiation changes emanating from the cavity caused by changes in an intensity, amplitude, phase, or amplitude and phase of the electro-magnetic radiation entering the cavity comprising measuring the intensity, amplitude, phase, or amplitude and phase of the sensed electro-magnetic radiation reflected off the entrance to the optical cavity and correcting the electro-magnetic radiation emanating from the cavity based on the measured intensity.

As previously described, at least some embodiments include tuning the wavelength of the beam of electro-magnetic radiation based on monitoring of a reference electromagnetic radiation exiting from a reference substance, wherein at least a portion of the electro-magnetic radiation reflected off the entrance to the optical cavity is passed through the reference substance, and wherein the reference substance is selected to insure that a frequency of the electro-magnetic radiation corresponds to a frequency at which an absorption of the substance is measured.

As previously described, at least some embodiments include tuning the beam of electro-magnetic radiation over the plurality of wavelengths one or multiple times, and recording the sensed electro-magnetic radiation at the plurality of wavelengths. As previously described, at least some embodiments include summing the recorded sensed electro-magnetic radiation for each of the plurality of wavelengths over the one or multiple times. As previously described, at least some embodiments include identifying repetitive patterns in the recorded sensed electro-magnetic radiation for each of the plurality of wavelengths over the one or multiple times. As previously described, at least some embodiments include detecting an amount of the substance based on the identified repetitive patterns in the summed recorded sensed electro-magnetic radiation for each of the plurality of wavelengths over the one or multiple times.

As previously described, at least some embodiments include receiving, by the processor, information from one or more detectors relating to a portion of the beam of electro-magnetic radiation not entering the cavity, wherein information received from the cavity detector and information received from one or more detectors are used to detect the substance.

Signature Generation

Figure 16:
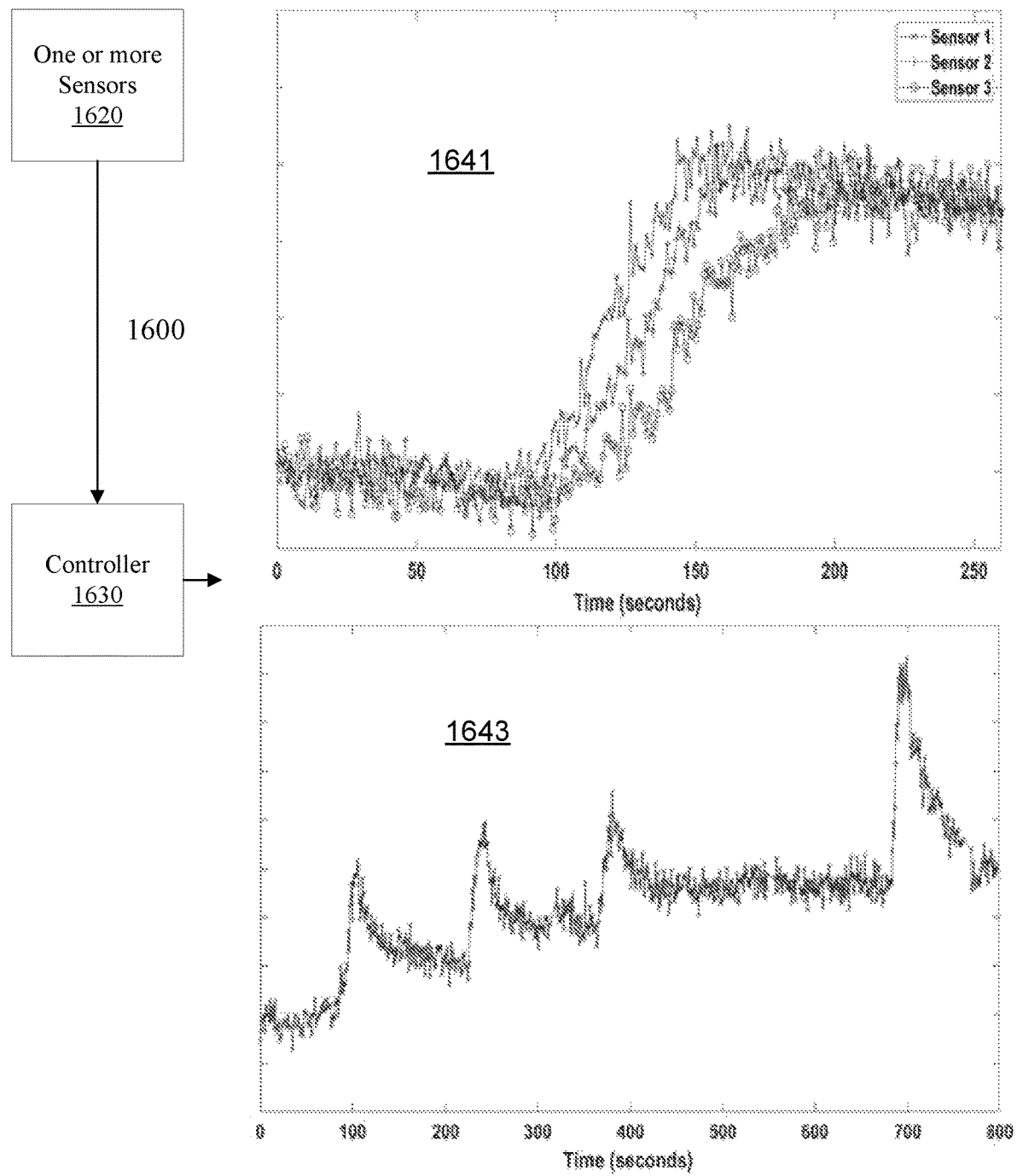
FIG. 16 shows a block diagram of a system for generating one or more signatures for one or more gas concentration conditions based on the sensed levels of gas over time, according to an embodiment.
Figure 17:
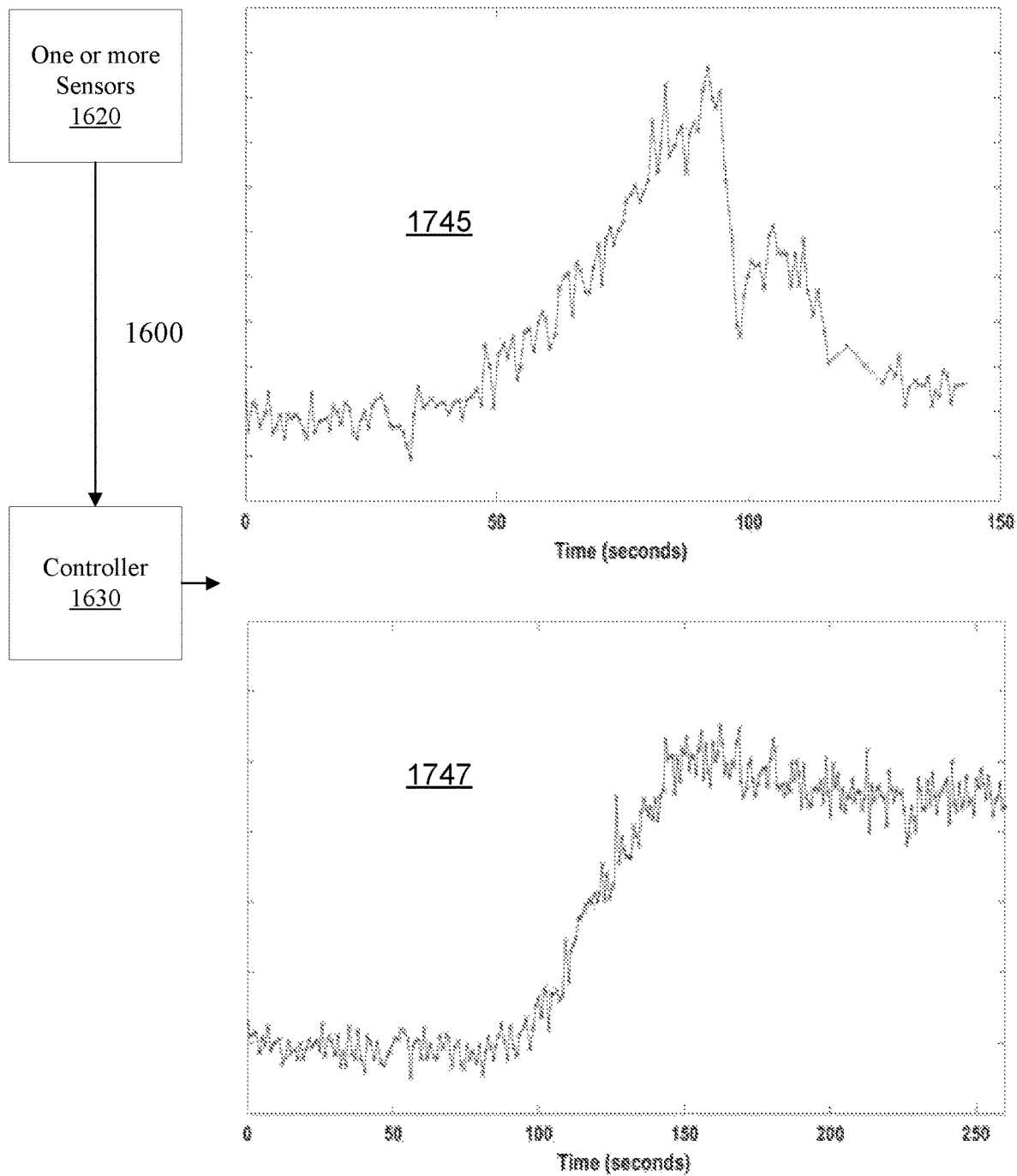
FIG. 17 shows a block diagram of a system for generating one or more signatures for one or more gas concentration conditions based on the sensed levels of gas over time, according to an embodiment.

FIG. 16 and FIG. 17 show a block diagram of a system 1600 for generating one or more signatures 1641, 6143, 1745, 1747 for one or more gas concentration conditions based on the sensed levels of gas over time, according to an embodiment. The system 1600 includes one or more sensors 1620 that sense gas. For an embodiment, the sensing of the gas is over a period of time (such as 250 seconds for signature 1641, 800 seconds for signature 1643, 150 seconds for signature 1745, and 250 seconds for signature 1747). The one or more sensors 1620 can include anyone of the previously described substance detection embodiments being used to detect gas. For an embodiment, one or more of the sensors includes the substance detection systems previously described.

A controller 1630 receives sensed values of gas concentrations from the one or more sensors 1620. Based on the sensed values of gas concentrations, the controller 1630 generates one or more signatures (such as, signatures 1641, 1643, 1745, 1747) which are composed of gas concentration data over time. For an embodiment, the controller 1630 is separate from the processor 140 of FIG. 1. For an embodiment, the controller 1630 is a first controller, and the processor 140 is a second controller or processor. The controller 1630 operates to generate the signatures, and the second controller (processor 140) operates to sense a substance or gas.

The signatures can be generated in many different ways. For an embodiment, signatures are generated by calibrating (predetermining) different possible gas concentration conditions. For example, a generic structure may be used as a calibration structure for future monitoring of gas concentration conditions of other structures. That is, signatures are generated for the generic structure, and in the future, other similar types of structures utilized the generated signatures for identifying gas concentration conditions.

For an embodiment, one or more sensors are deployed within a structure. For the structure, gas concentration conditions are monitored, and signatures of the gas concentration conditions are generated over time. For an embodiment, these signatures are then used for characterizing the gas concentration conditions of the structure.

For at least some embodiments, the signatures of a structure or structures are characterized over larger amounts of time. That is, for time periods greater than the previously mentioned period of time. For example, the signature(s) of a structure may depict repeating patterns over a duration of a day, week, month, or years. Deviations from characterized patterns of signatures can be used for identifying possible problems associated with gas concentration conditions.

Signature 1641 depicts sensed gas condition characterizing by three separate sensors. The separate sensors can be deployed within one or more structures. Signatures 1643, 1745, 1747 depict other exemplary characterized sensed gas conditions.

Figure 18:
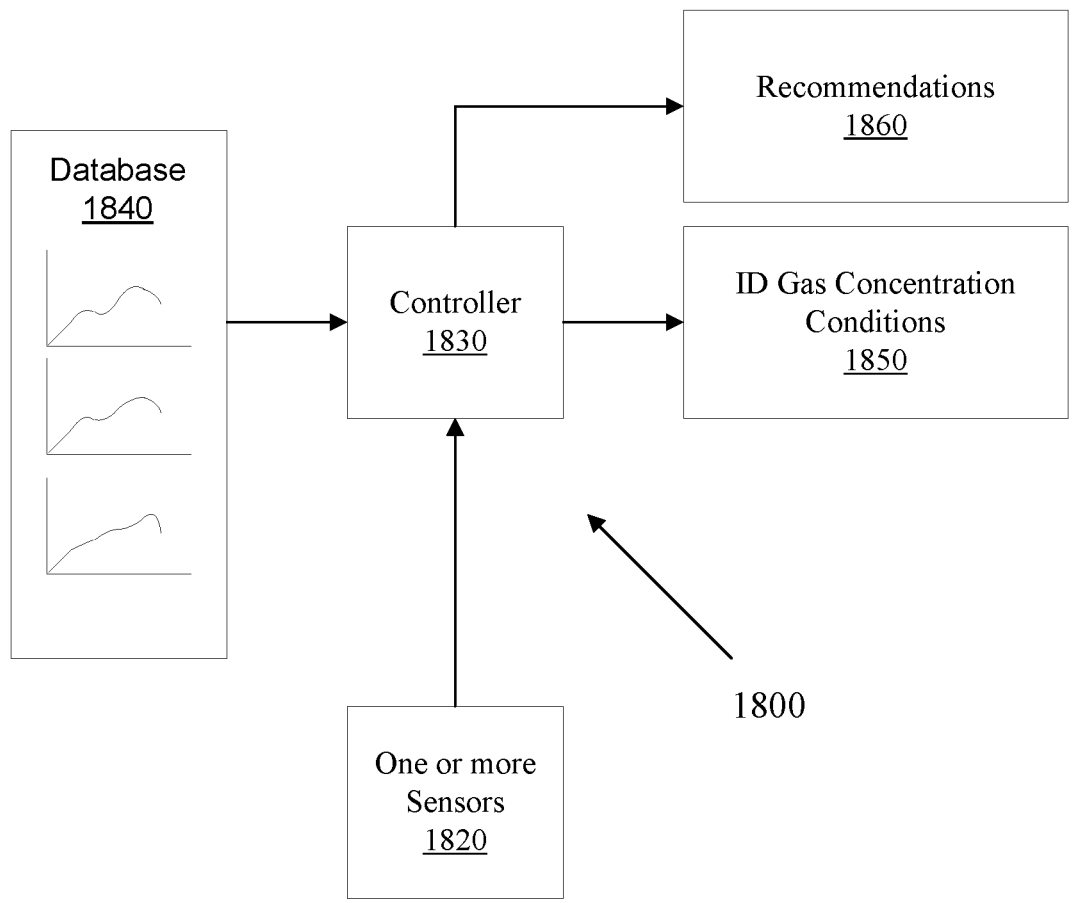
FIG. 18 is a block diagram of a system for identifying a gas concentration condition, according to an embodiment.

FIG. 18 is a block diagram of a system 1800 for identifying a gas concentration condition, according to an embodiment. For at least some embodiments, a controller 1830 generates recommendations 1860 or identifies gas concentration conditions 1850 by comparing sensed values of gas concentrations generated by one or more sensors 1820 with signatures stored in a database 1840. For an embodiment, the database 1840 is previously generated by storing signatures generated by previously sensed and or characterized gas concentrations.

For at least some embodiments, the sensed values of gas concentrations are added to the database 1840 to aid in the identifications of gas concentration conditions. Further, once the controller identifies a gas concentration condition, the controller can additionally provide recommendations. For example, the controller 1830 may identify a gas leak or valve that has been inadvertently left open. The gas leak or the open valve may be identified, and further, a recommendation may be provided that includes instructions to fix the leak or close the valve or respond to a potential safety threat.

For an embodiment, the system is included as a part of a larger system that may take action. For example, for an embodiment, the system may automatically close a valve or initiate a building alarm.

For another embodiment, the controller 1830 may identify the presence of unburned gas accumulating in or around ovens and ranges or any other appliances caused by the delayed ignitions of gas. The source of the gas may be identified, and further, a recommendation may be provided that includes a description of the source of the gas as a delayed ignition.

FIG. 19 is a flow chart that includes steps of a method of parameterizing recoded information related to detecting a gas, and an event or action related to the detecting of the gas, according to an embodiment. As stated, one or more sensors sense levels of a gas over time for a plurality of gas concentration conditions. As will be described, an embodiment of one or more of the sensors includes an optical cavity. A first step 1910 of FIG. 19 includes detecting a substance (gas) within an optical cavity based on at least one of an intensity, amplitude, a phase, or an amplitude and phase of sensed electro-magnetic radiation emanating from the optical cavity at one or more of a plurality of wavelengths while the optical cavity receives a beam of electro-magnetic radiation. A second step 1920 include recording, by a controller, information related to the detected substance (gas). A third step 1930 includes recording, by the controller, an event or action relating to the detected substance (gas). A fourth step 1940 includes describing or representing in terms of a parameter or parameters (parameterizing), by the controller, the recorded information and an event or action related to the detected substance (gas). Examples of methods for parameterizing recorded information and an event or action related to the detected substance include finding parametric equations of the recorded information and an event or action related to the detected substance defined by an implicit equation, parametric statistics based on parametrized families of probability distributions such as mean and variance, blob detection aimed at detecting regions in the recorded information and an event or action related to the detected substance that differ in properties compared to surrounding regions, edge detection aimed at identifying points in the recorded information and an event or action related to the detected at which the observables have discontinuities and maximum likelihood for estimating the parameters of a probability distribution by maximizing a likelihood function, so that under the assumed statistical model the observed data is most probable. It is to be understood that the examples given here are representative examples of methods to analyze data but is not to be taken as an exhaustive list. A fifth step 1950 includes recording, by the controller, the parameterized information in the database.

Figure 20:
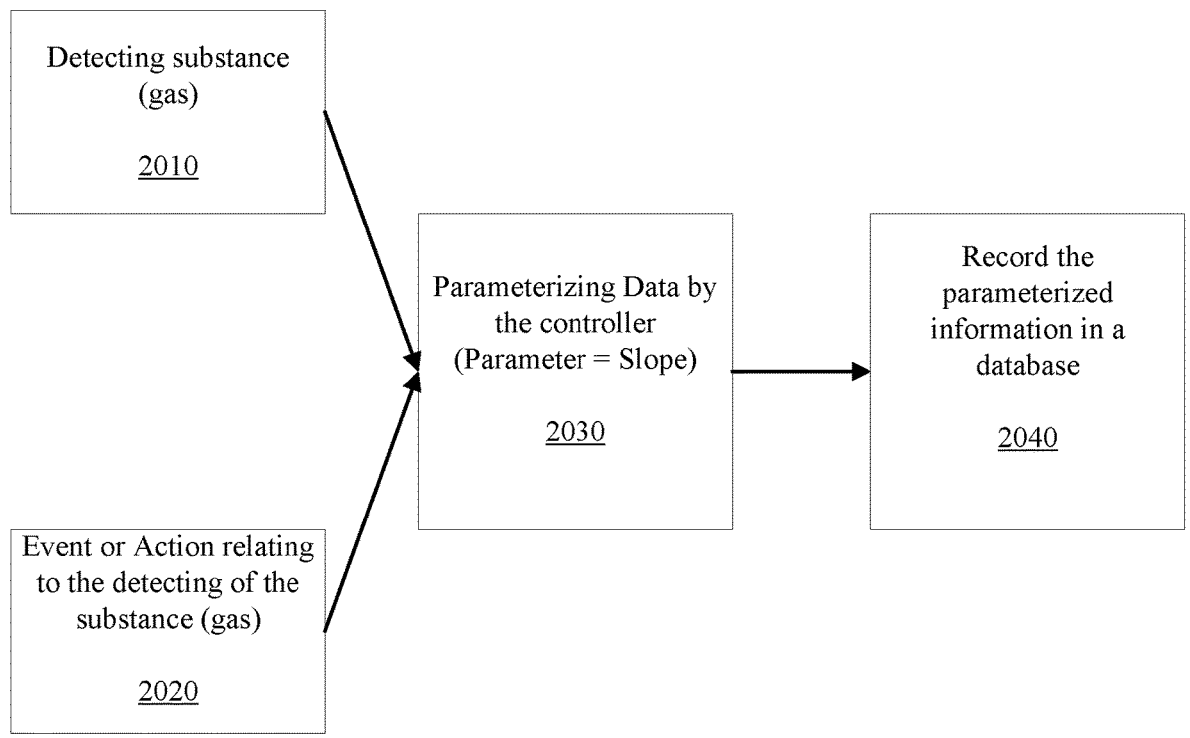
FIG. 20 is another chart that includes parameterizing recoded information related to detecting a gas, and an event or action related to the detecting of the gas, according to an embodiment.

FIG. 20 is another chart that includes parameterizing recoded information related to detecting a gas, and an event or action related to the detecting of the gas, according to an embodiment. A first step 2010 includes detecting a substance (gas). A second step 2020 includes identifying an event or action relating to the detecting of the substance (gas). A third step 2030 includes parameterizing data of the detected substance (gas) and the identified event or action. A fourth step 2040 includes recording the parameterized information in a database. For an embodiment, the parameter is a slope. For an embodiment, the slope represents a measure of the change in the detected substance over a time interval. For an embodiment, a positive slope denotes an increase in the detected substance over a time interval while for an embodiment, a negative slope denotes a decrease. The larger the value of the slope the greater the change in the detected substance verses time. By using the slope as a parameter, the change in detected substance over a time interval can be further characterized. By combining slope parameters over a plurality of time intervals, the behavior of the detected substance over longer time periods can be further characterized.

Figure 21:
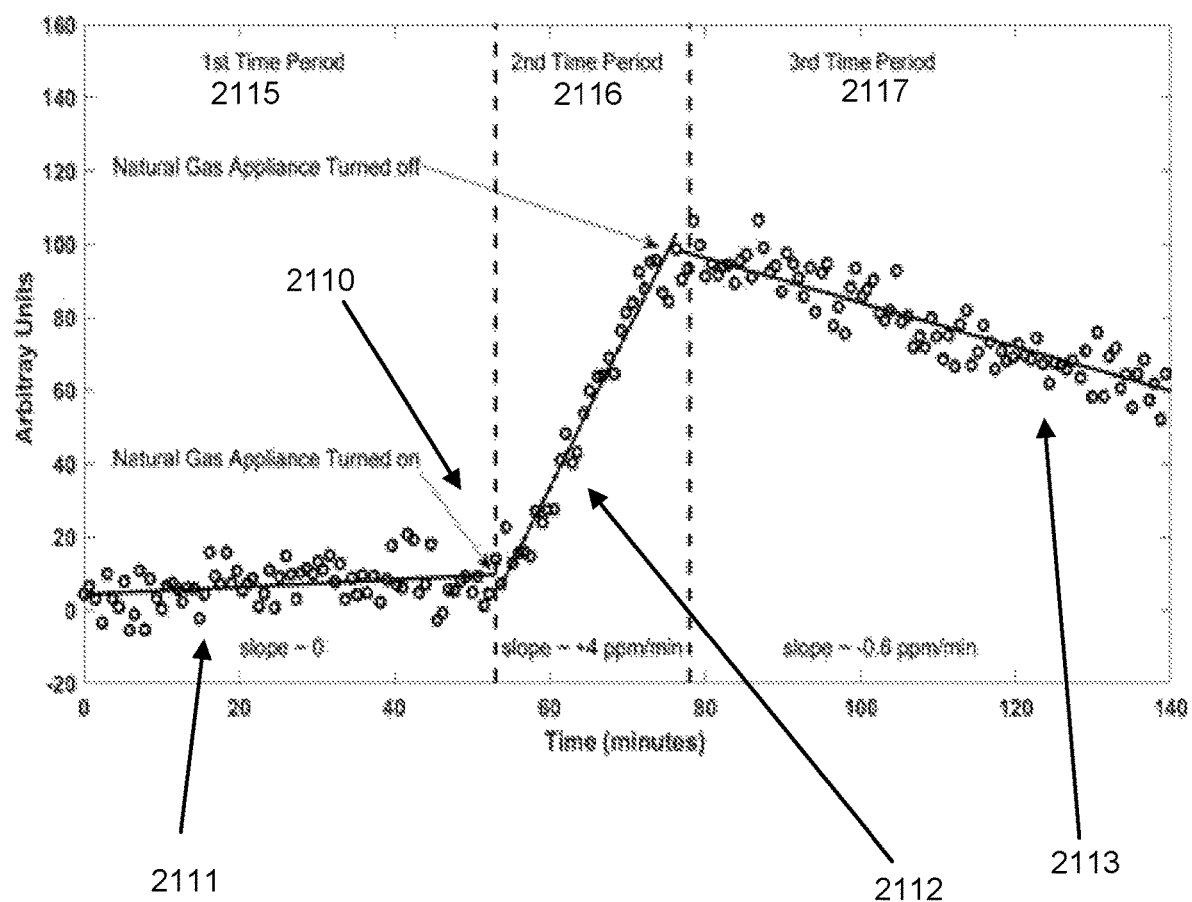
FIG. 21 shows a signature of detected gas that includes an association with one or more events or actions, according to an embodiment.

FIG. 21 shows a signature 2110 of detected gas that includes an association with one or more actions or events, according to an embodiment. As shown with the signature 2110 of FIG. 21, includes parameterized slopes 2111, 2112, 2113. As shown, time periods (first time period 2115, second time period 2116, third time period 2117) associated with the different slopes 2111, 2112, 2113 can provide indications of actions or events, such as, turning on a natural gas appliance within a structure, or turning off the natural gas appliance within the structure. As shown, for at least some embodiments, detecting the substance is parameterized as the change in natural gas concentration with respect to the change in time using a linear regression, which includes a process of determining a straight line that best approximates the data.

For an embodiment, the signature 2110 of FIG. 21 is a signature of detected gas that is associated with the operation of a natural gas tankless water heater. FIG. 21 shows the signature and linear regression associated with each of the three time periods (first time period 2115, second time period 2116, third time period 2117). The water heater is off for the first time period 2115, and the parameterized slope is approximately zero; meaning the change in natural gas over that first time period 2115 is approximately zero. Turning on the water heater starts the second time period 2116, and the parameterized slope is positive; meaning the concentration level of natural gas was increasing over the second time period 2116. Turning off the water heater starts the third time period 2117, and the parameterized slope is negative; meaning the concentration level of natural gas is decreasing. The different slopes 2111, 2112, 2113 provide indications of one or more actions or events associated with a natural gas tankless water heater. It is to be understood that the natural gas tankless water heater is one example of many possible gas sources.

Figure 22:
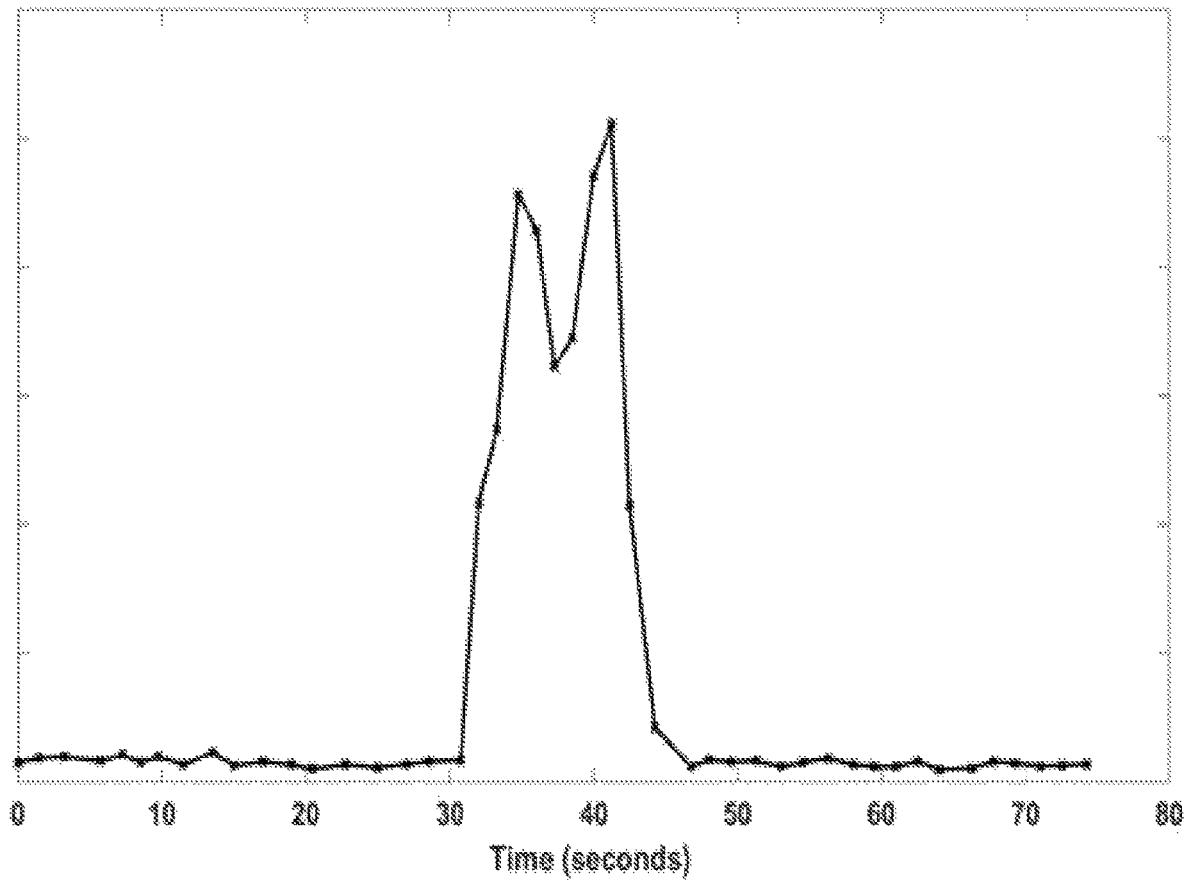
FIG. 22 shows a signature that includes detection of a gas concentration condition, in which an event or action is not necessary, according to an embodiment.

FIG. 22 shows a signature that includes detection of a gas concentration condition, in which an action is not necessary, according to an embodiment. As described, for at least some embodiments, the controller further parameterizes the received information relating to detecting the substance, parameterizes the measured data and outputs recommendations from a processor by comparing parameterized data with a database of signatures. In some cases, the substance is measured but because of the nature of the information related to detecting the substance, and notification may be unnecessary and the determination is made not to take action. An example could include a situation in which a transitory plume of natural gas is detected. However, the transitory plume may be of no concern because, for example, it presents no danger. If the plume presents no danger, a notification is unnecessary. This may be determined by comparing the sensed gas condition with the signature of the transitory plume.

Figure 23:
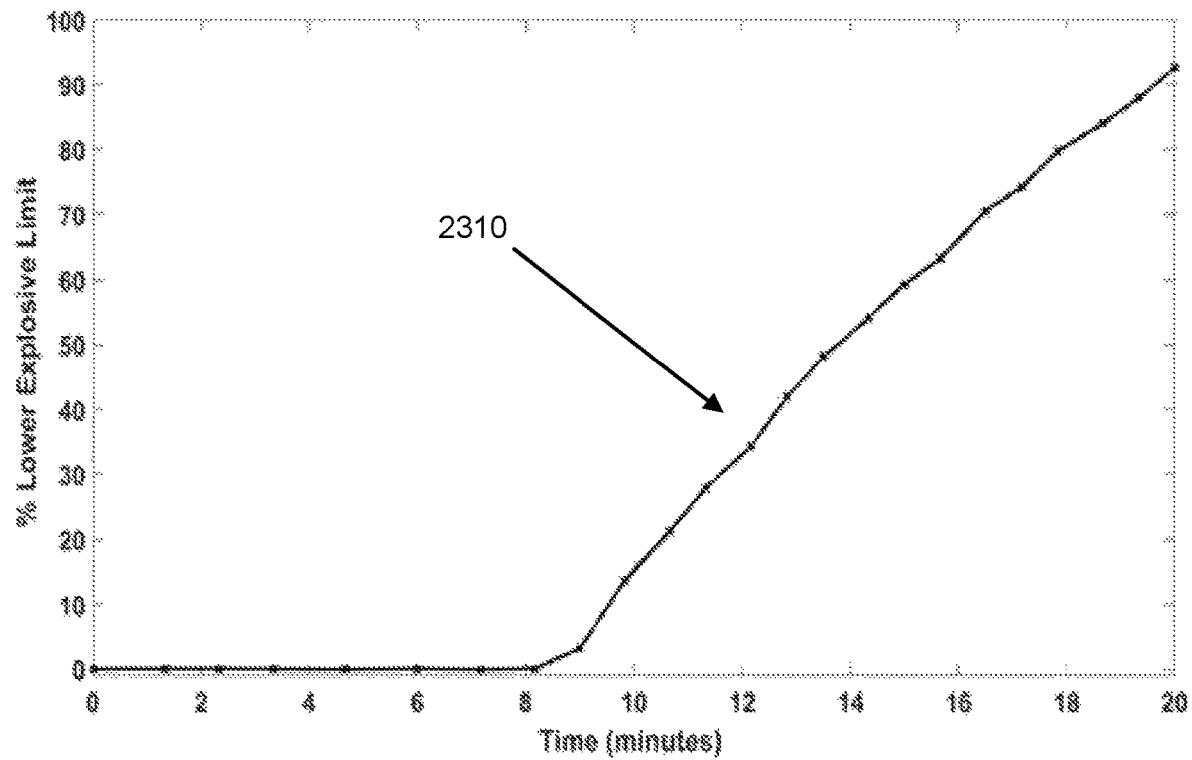
FIG. 23 shows a signature that includes detection of a gas concentration condition in which an event or action may be necessary, according to an embodiment.

FIG. 23 shows a signature 2310 that includes detection of a gas concentration condition in which an action may be necessary, according to an embodiment. The signature 2310 indicates that an action should be taken based on the characteristics of the signature 2310. This signature 2310 may indicate an action should be taken to limit the sensed level of gas as the sensed level approaches a Lower Explosion Limit (LEL).

Figure 24:
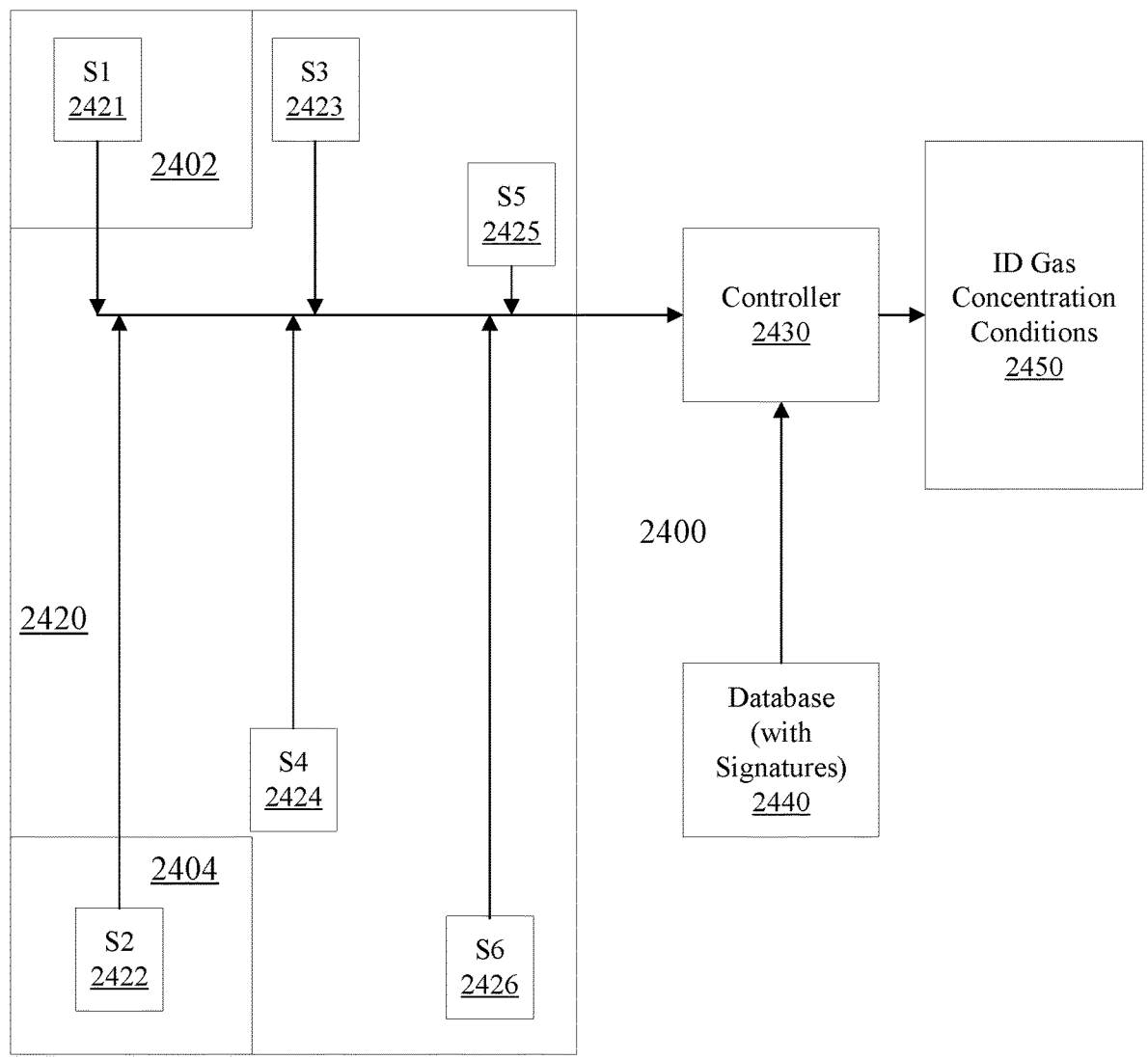
FIG. 24 is a block diagram of a system that includes a plurality of sensors distributed within a structure, wherein the plurality of sensors generate sensed levels of gas over time, and one or more gas concentrations conditions of the structure are identified based on the generated signatures and the sensed levels of gas generated by the plurality of sensors distributed within the structure, according to an embodiment.

FIG. 24 is a block diagram of a system 2400 that includes a plurality of sensors 2421, 2422, 2423, 2424, 2425, 2426 distributed within a structure 2420, wherein the plurality of sensors 2421, 2422, 2423, 2424, 2425, 2426 generate sensed levels of gas over time, and one or more gas concentrations conditions 2450 of the structure 2420 are identified based on the generated signatures and the sensed levels of gas generated by the plurality of sensors 2421, 2422, 2423, 2424, 2425, 2426 distributed within the structure 2420, according to an embodiment. As shown, a controller 2430 receives the sensed values of the sensors 2421, 2422, 2423, 2424, 2425, 2426 and compares the sensed values to signatures previously stored in a database 2440.

The structure 2420 can include multiple substructures 2402, 2404 (such as, rooms within the structure 2420. For example, gas from an interior leak located in a kitchen can disperse throughout a structure. It takes time for gas to disperse (propagate) from one location to another within a structure. If a plurality of sensors is distributed within a structure, at any point in time, the signature of each of the sensors can be very different. For example, the signature(s) associated with a kitchen can be substantially different than the signature(s) associated with a bedroom.

Figure 25:
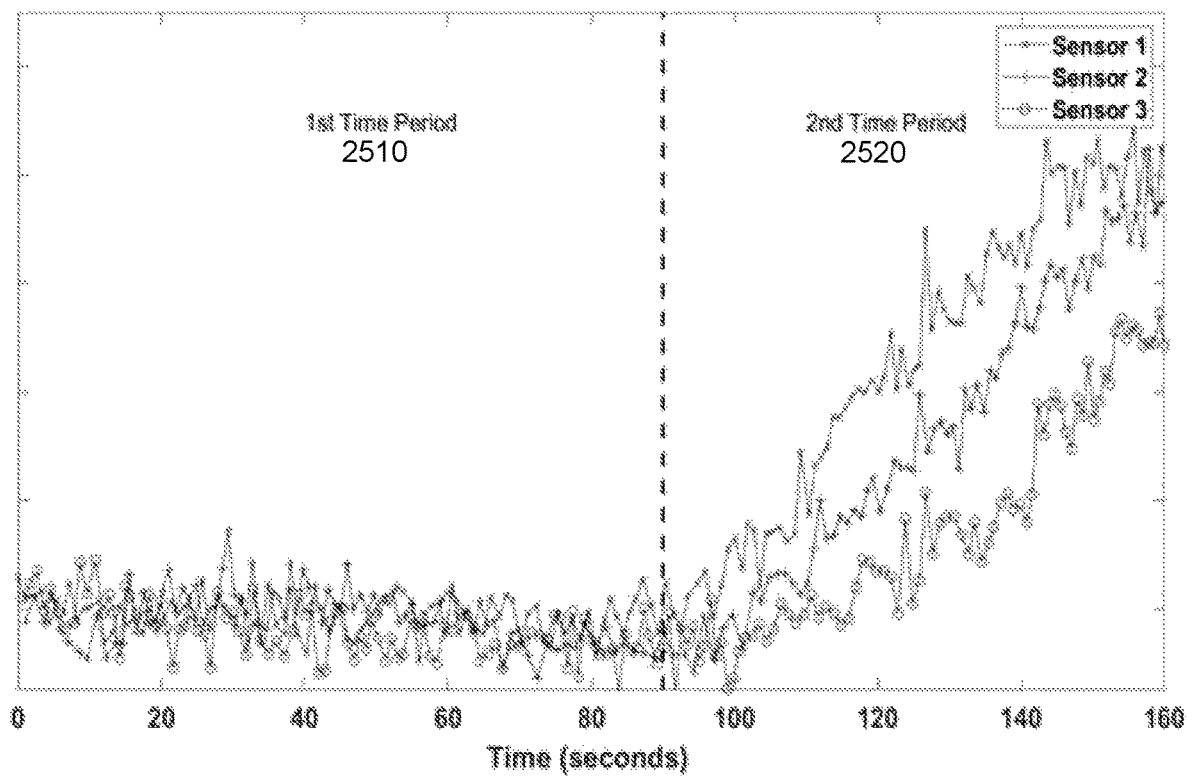
FIG. 25 shows signatures that include the detection of gas concentration conditions at three substructures, according to an embodiment.

FIG. 25 shows signatures that include the detection of gas concentration conditions at three substructures, according to an embodiment. The gas originates from a gas leak located near the substructure containing Sensor 1. Sensor 2 is located in a substructure located farther from the gas leak while Sensor 3 is located in a substructure farthest from the leak. The slopes of all three signatures in the first time period 2510 are approximately zero; indicating a change in natural gas over time of approximately zero. During the time interval in which the gas was turned on (second time period 2520), all three slopes are positive. The slope of Sensor 1 is the largest followed by the slope of Sensor 2, whereas the slope of Sensor 3 is the smallest. Because it takes time for gas to disperse, a larger slope can indicate a sensor with closer proximity to the leak then a sensor with a smaller slope because it takes time for the gas to disperse, thus possibly providing a leak location notification.

Figure 26:
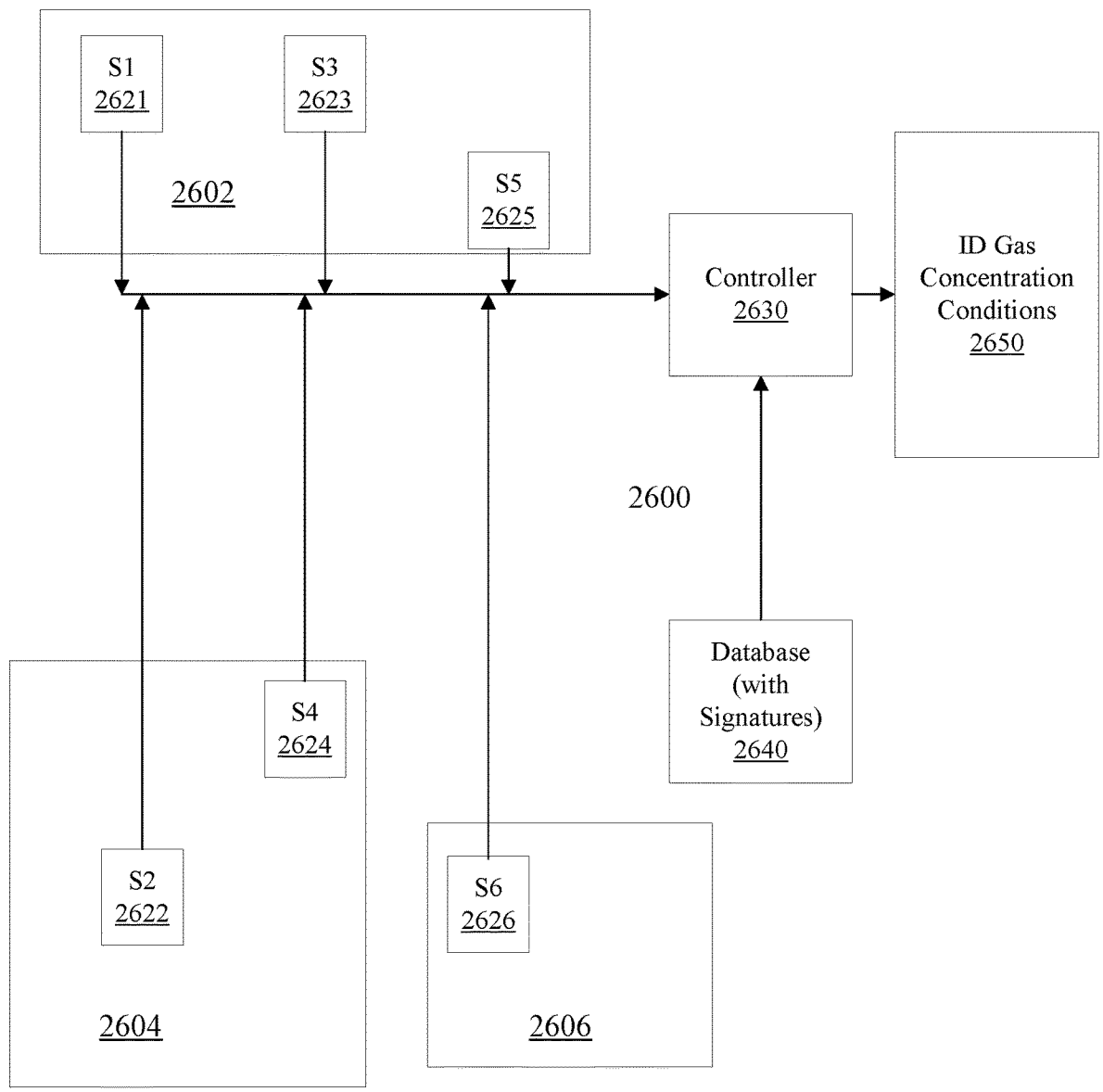
FIG. 26 is a block diagram of a system that includes a plurality of sensors distributed within a plurality of physically different structures, wherein the plurality of sensors generate sensed levels of gas over time, and one or more gas concentrations conditions are identified based on the generated signatures and the sensed levels of gas generated by the plurality of sensors distributed within the plurality of physically different structures, according to an embodiment.

FIG. 26 is a block diagram of a system 2600 that includes a plurality of sensors distributed within a plurality of physically different structures 2602, 2604, 2606, wherein the plurality of sensors 2621, 2622, 2623, 2624, 2625, 2626 generate sensed levels of gas over time, and one or more gas concentrations conditions are identified based on the generated signatures and the sensed levels of gas generated by the plurality of sensors 2621, 2622, 2623, 2624, 2625, 2626 distributed within the plurality of physically different structures, according to an embodiment. For example, it is possible to over pressurize main gas pipelines (such as the explosive event that occurred Merrimack Valley Gas explosion on Sep. 13, 2018) having distributing pipes extending to a plurality of physically different structures, such as homes/buildings and factories. Sensors distributed within a plurality of physically different structures may identify this gas concentration condition as main gas pipeline problem based on the generated signatures and the sensed levels of gas generated within a plurality of physically different structures wherein notifications to the proper authorities may be necessary.

The sensed values generated by the sensors 2621, 2622, 2623, 2624, 2625, 2626 are received by a controller 2630 that compares the sensed values with signatures stored in database 2640, and identifies one or more gas concentration conditions 2650.

Figure 27:
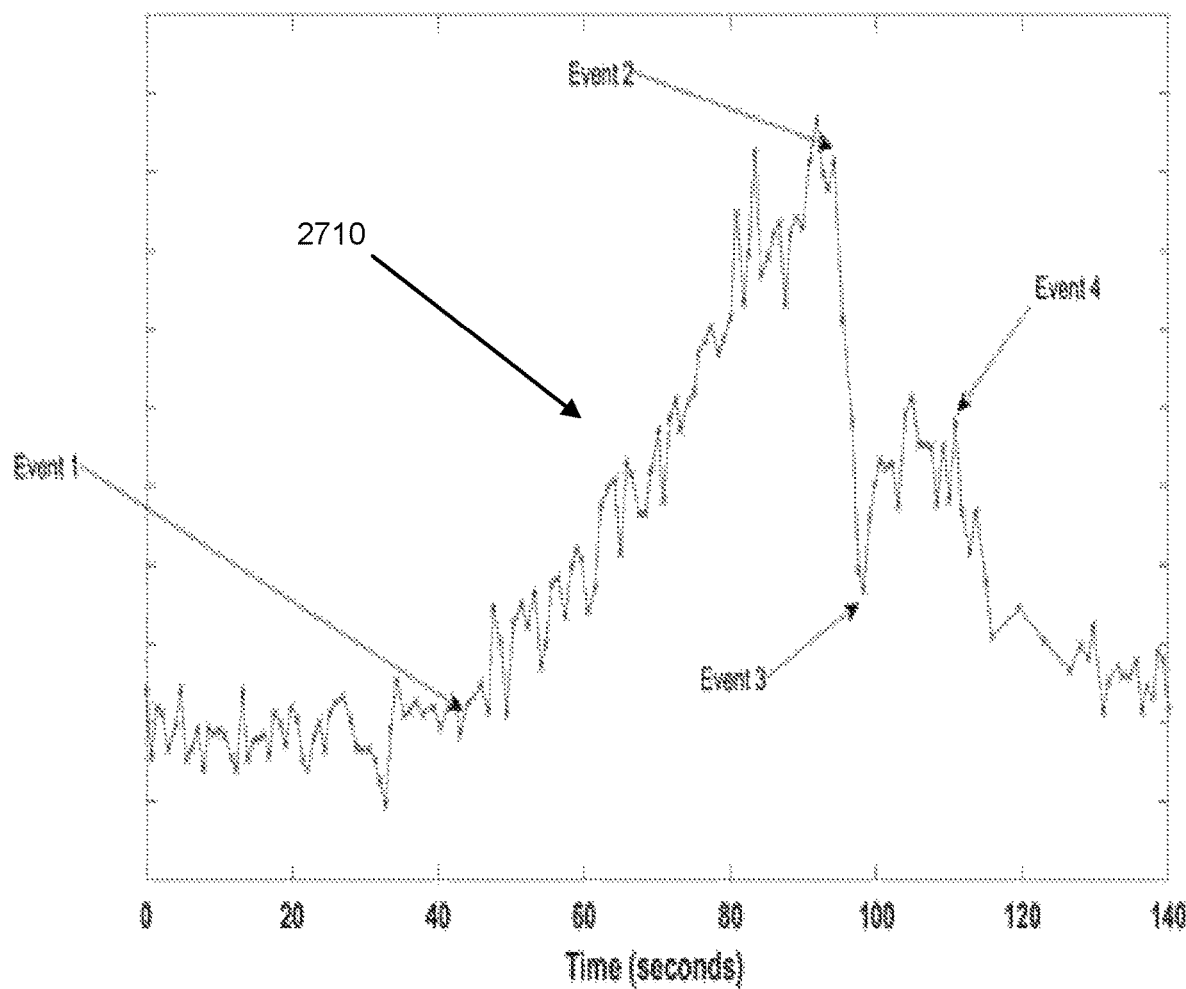
FIG. 27 shows a signature and a timing of actions or events (Event 1, Event 2, Event 3, Event 4) that are observed to be associated with characteristics of the signature, according to an embodiment.

FIG. 27 shows a signature 2710 and a timing of actions or events (Event 1, Event 2, Event 3, Event 4) that are observed to be associated with characteristics of the signature 2710, according to an embodiment. These actions or events may include, for example, the steps in replacing a natural gas appliance in a structure. Event 1 may be the disconnection of the gas line feeding the natural gas appliance to be replaced. This process may release gas into a structure. The signature associated with Event 1 being increases in the concentration levels of gas. Event 2 may be connecting the gas line to the replacement natural gas appliance (gas is no longer leaking from the gas line). The signature associated with Event 2 being decreasing concentration levels of gas. Event 3 may be turning on the replacement natural gas appliance generating a gas leak associated with the operation of the replacement appliance. The signature associated with Event 3 being increases in the concentration level of gas. Event 4 may be repairing the gas leak in the replacement natural gas appliance. The signature associated with Event 4 being decreases in the concentration level of gas. The actions or events can be correlated with features of the signatures. Accordingly, actions or events can be identified as having occurred by analyzing the signatures.

Figure 28:
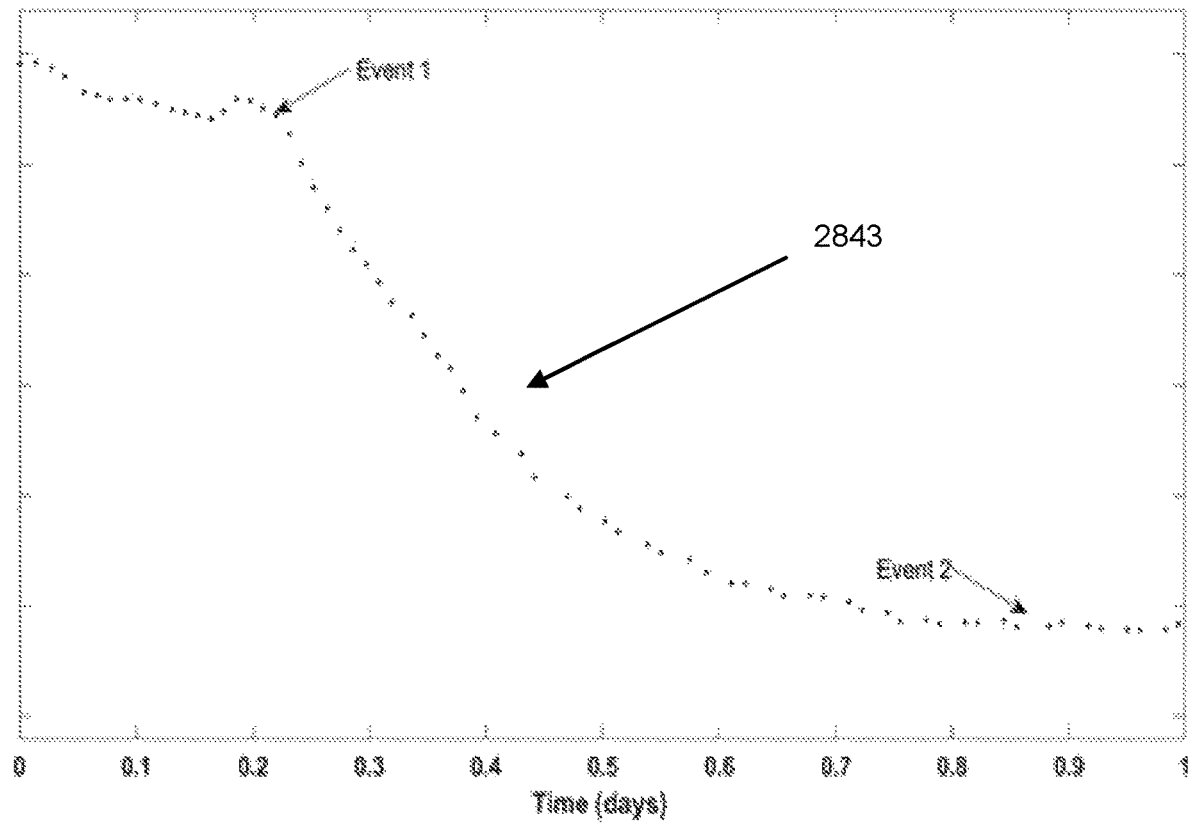
FIG. 28 shows a signature and a timing of actions or events (Event 1, Event 2) that are observed to be associated with characteristics of the signature, according to an embodiment.

FIG. 28 shows a signature 2843 and a timing of actions or events (Event 1, Event 2) that are observed to be associated with characteristics of the signature 2843, according to an embodiment. These actions or events may include, for example, steps in identifying and mitigating high concentrations of gas in a commercial facility such as a restaurant or commissary. The signature associated with the action or Event 1 may indicate a high concentration levels of gas. The action or Event 1 may include turning on ventilation fans, letting outside air into the structure. Action or Event 2 may include turning off the ventilation fans in the structure. The signature associated with action or Event 2 may indicate lower concentration levels of gas.

FIG. 29 is a flow chart that include steps of a method of generating a plurality of signatures, wherein one or more signatures is generated for one or more gas concentration conditions based on the sensed levels of gas over time, according to an embodiment. A first step 2910 includes sensing, by one or more sensors, levels of a gas over time for a plurality of gas concentration conditions. A second step 2920 includes receiving, by a controller, the sensed levels of gas over time for the plurality of gas concentration conditions. A third step 2930 includes generating, by the controller, a plurality of signatures, wherein one or more signatures is generated for one or more gas concentration conditions based on the sensed levels of gas over time.

At least some embodiments further include determining, by the controller, whether to take action or not to take action. Examples of actions taken include turning off a valve, alarming, and/or communicating a notification. Examples of not taking an action include not taking an action because if a determination that there is no safety or no environmental impact.

At least some embodiments further include sensing in real-time, by the one or more sensors, present levels of gas over time, and identifying a present gas concentration condition based on the sensed in real-time levels of gas over time and at least one of the plurality of signatures. For an embodiment, the present levels of gas are compared with the signatures, and the present gas concentration is identified based on the comparison. For an embodiment, the present levels of gas sensed over time are added to a database of signatures, thereby adding a higher level of information to the database.

For at least some embodiments, at least one of the plurality of signatures includes a rate of change of sensed levels of gas over time. The rate of change of the sense levels is useful because the rate of change can be an indicator of the emergency response time needed to avert fatalities, injuries, property damage, litigation and other costs associated with natural gas related fires and explosions. The rate of change may be represented by a slope that represents a measure of the change in the detected substance (gas) over a time interval. As previously described, for an embodiment, a positive slope denotes an increase in the detected substance over a time interval while for an embodiment, a negative slope denotes a decrease. The larger the value of the slope the greater the change in the detected substance verses time. By using the slope as a parameter, the change in detected substance over a time interval can be further characterized. As previously described, by combining slope parameters over a plurality of time intervals, the behavior of the detected substance over longer time periods can be further characterized.

At least some embodiments further include storing, by the controller, the signatures generated for each of the gas concentration conditions. The signature can be stored locally, or the signatures can be stored, for example, in the cloud, and be available for systems located elsewhere.

At least some embodiments further include retrieving one or more signatures when identifying a present gas concentration condition. The signatures can be retrieved locally, or from the cloud.

For at least some embodiments, each of the plurality of gas concentrations conditions are controlled, and a corresponding signature is generated to allow for later real-time detection of each of the plurality of gas concentrations conditions. That is, gas conditions of, for example, a structure are controlled to simulate certain conditions. The signatures are then accordingly generated. Later, the gas concentration conditions can be sensed, and conclusions can be made about the sensed gas concentration conditions. Essentially, a structure can be calibrated to determine the sensed gas conditions for different possible conditions.

Figure 30:
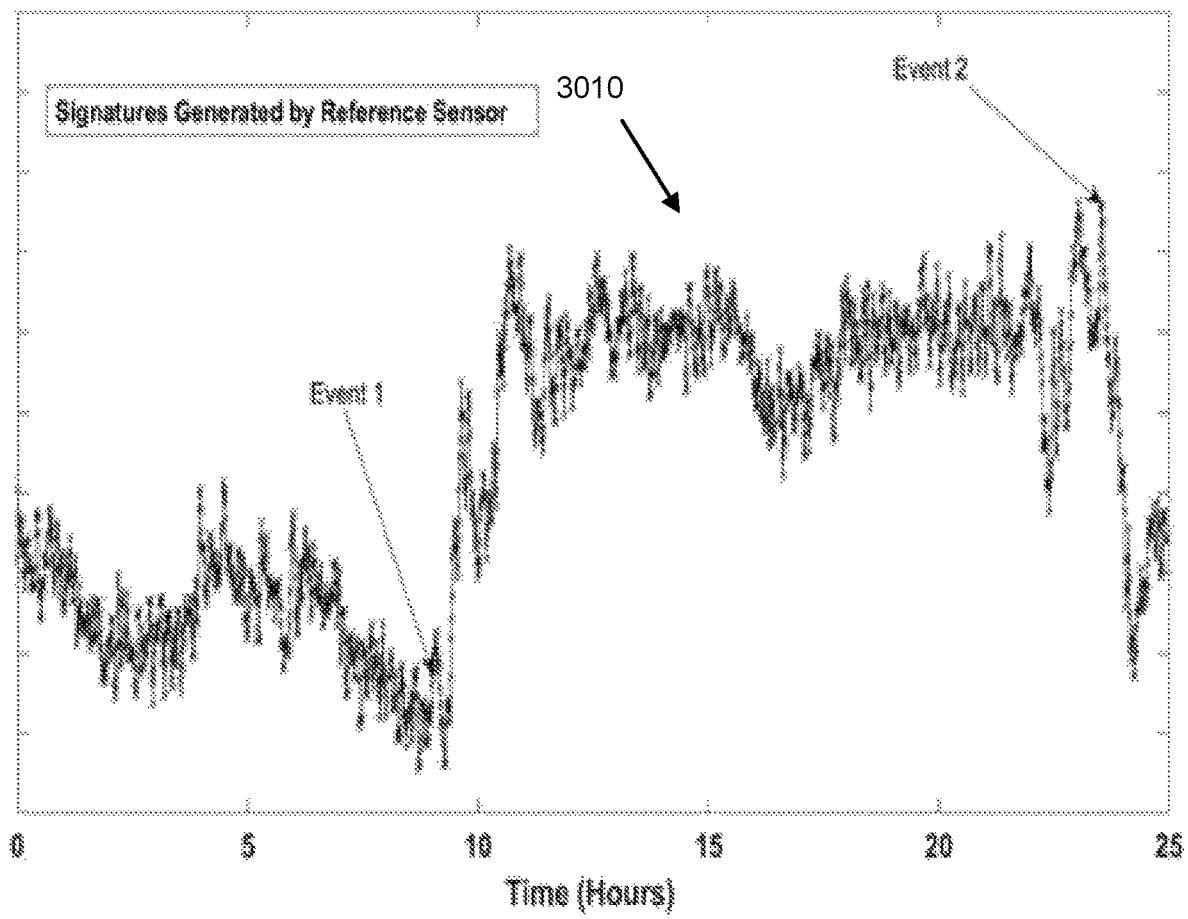
FIG. 30 shows a signature generated by a reference sensor associated with gas concentrations conditions that are controlled by an event or action and an event or action, according to an embodiment.

FIG. 30 shows a signature 3010 generated by a reference sensor associated with gas concentrations conditions that are controlled by an action or Event 1 and an action or Event 2, according to an embodiment.

Figure 31:
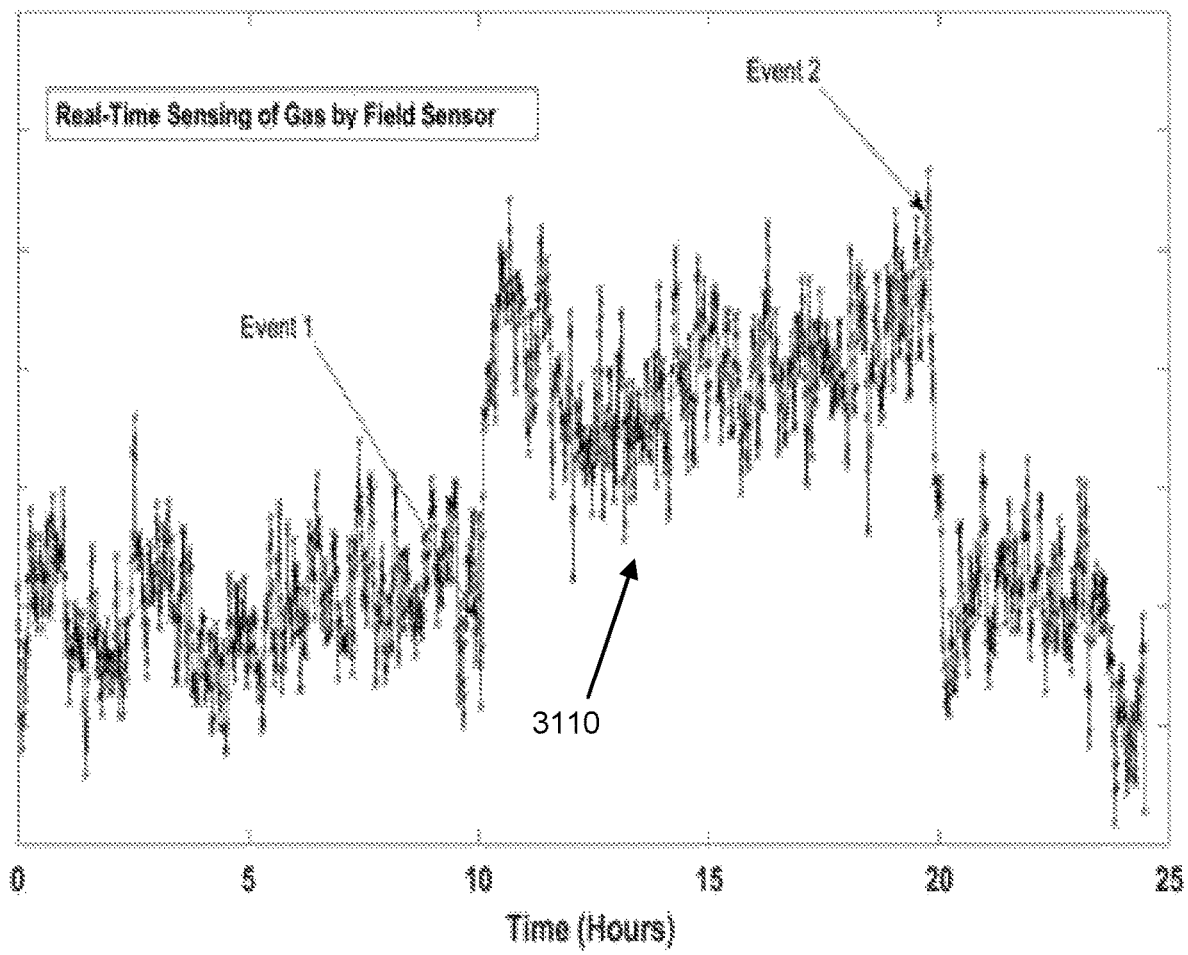
FIG. 31 shows a signature generated by a field sensor at a later point in time associated with gas concentrations conditions that are controlled by an event or action, according to an embodiment.

FIG. 31 shows a signature 3110 generated by a field sensor at a later point in time (later than the signature generated in FIG. 30) associated with gas concentrations conditions that are controlled by an action or Event 1 and an action or Event 2, according to an embodiment. While at a later point in time, the gas concentration conditions can be sensed as shown in FIG. 31. Conclusions can be made about the sensed gas concentration conditions based on a comparison of the signature shown in FIG. 31 with the previously generated signature shown in FIG. 30. Based on a comparison, action or Event 1 and action or Event 2 may have taken place at a later point in time. For at least some embodiments, the one or more sensors include a plurality of sensors, and wherein one or more reference sensors are used to generate the signatures, and one or more field sensors are used to detect one or more of the plurality of gas concentrations conditions based upon the signatures and real-time sensing of gas by the one or more field sensors. That is, the reference sensors may be used to initially generate the signatures. Later, a different (field) sensor(s) generate sensed gas conditions that are compared with the previously generated signature.

As previously described, for at least some embodiments, the one or more sensors includes a plurality of sensors distributed within a structure, and wherein the plurality of sensors generate sensed levels of gas over time, and one or more gas concentrations conditions of the structure are identified based on the generated signatures and the sensed levels of gas generated by the plurality of sensors distributed within the structure.

As previously described, for at least some embodiments, the one or more sensors includes a plurality of sensors distributed within a plurality of physically different structures, and wherein the plurality of sensors generate sensed levels of gas over time, and one or more gas concentrations conditions are identified based on the generated signatures and the sensed levels of gas generated by the plurality of sensors distributed within the plurality of physically different structures.

At least some embodiments include identifying an association between an action and characteristics of the at least one of the plurality of signatures. At least some embodiments include identifying an association between an action and characteristics of the at least one of the plurality of signatures over time. For at least some embodiments identifying the association between the action and the characteristics of the at least one of the plurality of signatures comprises correlating the action with the characteristics of the at least one of the plurality of signatures.

As previously described in much greater detail, for an embodiment, at least one of the one or more sensors includes a tunable light source wherein the tunable light source generates a beam of electro-magnetic radiation, wherein a wavelength of the beam of electro-magnetic radiation is tuned to operate at a plurality of wavelengths, an optical cavity, wherein the optical cavity receives the beam of electro-magnetic radiation, wherein physical characteristics of the optical cavity define a plurality of allowed axial-plus-transverse electro-magnetic radiation modes, wherein only a subset of the plurality of allowed axial-plus-transverse electro-magnetic radiation modes are excited when the optical cavity receives the beam of electro-magnetic radiation, and a cavity detector, wherein the cavity detector senses electro-magnetic radiation emanating from the optical cavity. Further, information relating to the sensed electro-magnetic radiation is received from the one or more sensors, and gas within the optical cavity is detected based on at least one of an intensity, an amplitude, a phase, or an amplitude and phase of the sensed electro-magnetic radiation emanating from the optical cavity at one or more of the plurality of wavelengths while the optical cavity receives the beam of electro-magnetic radiation.

Although specific embodiments have been described and illustrated, the embodiments are not to be limited to the specific forms or arrangements of parts so described and illustrated. The described embodiments are to only be limited by the claims.

What is claimed:

1. A method, comprising:
    sensing, by one or more sensors, levels of a gas over time for a plurality of gas concentration conditions;
    receiving, by a controller, the sensed levels of gas over time for the plurality of gas concentration conditions; and
    generating, by the controller, a plurality of signatures, wherein one or more signatures is generated for one or more gas concentration conditions based on the sensed levels of gas over time;
    wherein at least one of the one or more sensors comprises:
    a tunable light source wherein the tunable light source generates a beam of electro-magnetic radiation, wherein a wavelength of the beam of electro-magnetic radiation is tuned to operate at a plurality of wavelengths;
    an optical cavity, wherein the optical cavity receives the beam of electro-magnetic radiation, wherein physical characteristics of the optical cavity define a plurality of allowed axial-plus-transverse electro-magnetic radiation modes, wherein only a subset of the plurality of allowed axial-plus-transverse electro-magnetic radiation modes are excited when the optical cavity receives the beam of electro-magnetic radiation;
    a cavity detector, wherein the cavity detector senses electro-magnetic radiation emanating from the optical cavity;
    and further comprising:
        receiving information relating to the sensed electro-magnetic radiation;
        detecting gas within the optical cavity based on at least one of an intensity, an amplitude, a phase, or an amplitude and phase of the sensed electro-magnetic radiation emanating from the optical cavity at one or more of the plurality of wavelengths while the optical cavity receives the beam of electro-magnetic radiation.

2. The method of claim 1, further comprising:
    determining, by the controller, whether to take action or not to take action.

3. The method of claim 1, further comprising:
    sensing in real-time, by the one or more sensors, present levels of gas over time;
    identifying a present gas concentration condition based on the sensed in real-time levels of gas over time and at least one of the plurality of signatures.

4. The method of claim 1, wherein at least one of the plurality of signatures includes a rate of change of sensed levels of gas over time.

5. The method of claim 1, further comprising:
    storing, by the controller, the signatures generated for each of the gas concentration conditions.

6. The method of claim 5, further comprising retrieving one or more signatures when identifying a present gas concentration condition.

7. The method of claim 1, wherein each of the plurality of gas concentrations conditions are controlled, and a corresponding signature is generated to allow for later real-time detection of each of the plurality of gas concentrations conditions.

8. The method of claim 1, wherein the one or more sensors include a plurality of sensors, and wherein one or more reference sensors are used to generate the signatures, and one or more field sensors are used to detect one or more of the plurality of gas concentrations conditions based upon the signatures and real-time sensing of gas by the one or more field sensors.

9. The method of claim 1, wherein the one or more sensors includes a plurality of sensors distributed within a structure, and wherein the plurality of sensors generate sensed levels of gas over time, and one or more gas concentrations conditions of the structure are identified based on the generated signatures and the sensed levels of gas generated by the plurality of sensors distributed within the structure.

10. The method of claim 1, wherein the one or more sensors includes a plurality of sensors distributed within a plurality of physically different structures, and wherein the plurality of sensors generate sensed levels of gas over time, and one or more gas concentrations conditions are identified based on the generated signatures and the sensed levels of gas generated by the plurality of sensors distributed within the plurality of physically different structures.

11. The method of claim 1, further comprising identifying an association between an action or event and characteristics of the at least one of the plurality of signatures.

12. The method of claim 11, further comprising identifying an association between an action or event and characteristics of the at least one of the plurality of signatures over time.

13. The method of claim 11, wherein identifying the association between the action or event and the characteristics of the at least one of the plurality of signatures comprises correlating the action or event with the characteristics of the at least one of the plurality of signatures.

14. A system, comprising:
    one or more sensors operative to sense levels of a gas over time for a plurality of gas concentration conditions;
    a controller, the controller operative to:

receive the sensed levels of gas over time for the plurality of gas concentration conditions; and generate a plurality of signatures, wherein one or more signatures is generated for one or more gas concentration conditions based on the sensed levels of gas over time;

wherein at least one of the one or more sensors comprises:
a tunable light source wherein the tunable light source generates a beam of electro-magnetic radiation, wherein a wavelength of the beam of electro-magnetic radiation is tuned to operate at a plurality of wavelengths;
an optical cavity, wherein the optical cavity receives the beam of electro-magnetic radiation, wherein physical characteristics of the optical cavity define a plurality of allowed axial-plus-transverse electro-magnetic radiation modes, wherein only a subset of the plurality of allowed axial-plus-transverse electro-magnetic radiation modes are excited when the optical cavity receives the beam of electro-magnetic radiation;
a cavity detector, wherein the cavity detector senses electro-magnetic radiation emanating from the optical cavity;
and further comprising:
receiving information relating to the sensed electro-magnetic radiation;

detecting gas within the optical cavity based on at least one of an intensity, an amplitude, a phase, or an amplitude and phase of the sensed electro-magnetic radiation emanating from the optical cavity at one or more of the plurality of wavelengths while the optical cavity receives the beam of electro-magnetic radiation.

15. The system of claim 14, wherein the one or more sensors operate to sense in real-time, by present levels of gas over time, and the controller operates to identify a present gas concentration condition based on the sensed in real-time levels of gas over time and at least one of the plurality of signatures.

16. The system of claim 14, wherein the controller further operates to store the signatures generated for each of the gas concentration conditions.

17. The system of claim 16, wherein the controller further operates to retrieve one or more signatures when identifying a present gas concentration condition.

18. The system of claim 14, wherein the one or more sensors includes a plurality of sensors distributed within a structure, and wherein the plurality of sensors generate sensed levels of gas over time, and one or more gas concentrations conditions of the structure are identified based on the generated signatures and the sensed levels of gas generated by the plurality of sensors distributed within the structure.

19. The system of claim 14, wherein the one or more sensors includes a plurality of sensors distributed within a plurality of physically different structures, and wherein the plurality of sensors generate sensed levels of gas over time, and one or more gas concentrations conditions are identified based on the generated signatures and the sensed levels of gas generated by the plurality of sensors distributed within the plurality of physically different structures.

20. The system of claim 14, wherein the controller further operates to identify an association between an event or action and characteristics of the at least one of the plurality of signatures.

21. A system, comprising:
one or more sensors operative to sense levels of a gas over time for a plurality of gas concentration conditions, at least one of the one or more sensors comprising:
a tunable light source wherein the tunable light source generates a beam of electro-magnetic radiation, wherein a wavelength of the beam of electro-magnetic radiation is tuned to operate at a plurality of wavelengths;
an optical cavity, wherein the optical cavity receives the beam of electro-magnetic radiation, wherein physical characteristics of the optical cavity define a plurality of allowed axial-plus-transverse electro-magnetic radiation modes, wherein only a subset of the plurality of allowed axial-plus-transverse electro-magnetic radiation modes are excited when the optical cavity receives the beam of electro-magnetic radiation;
a cavity detector, wherein the cavity detector senses electro-magnetic radiation emanating from the optical cavity;
wherein a first controller further operates to:
receive information relating to the sensed electro-magnetic radiation;
detect gas within the optical cavity based on at least one of an intensity, an amplitude, a phase, or an amplitude and phase of the sensed electro-magnetic radiation emanating from the optical cavity at one or more of the plurality of wavelengths while the optical cavity receives the beam of electro-magnetic radiation;
the system further comprising:
a second controller, the second controller operative to:
receive the sensed levels of gas over time for the plurality of gas concentration conditions; and
generate a plurality of signatures, wherein one or more signatures is generated for one or more gas concentration conditions based on the sensed levels of gas over time.

* * * * *